(12) United States Patent
Striegler

(10) Patent No.: US 10,870,103 B2
(45) Date of Patent: Dec. 22, 2020

(54) CHIRAL BINUCLEAR METAL COMPLEXES FOR STEREOSELECTIVE HYDROLYSIS OF SACCHARIDES AND GLYCOSIDES

(71) Applicant: BOARD OF TRUSTEES OF THE UNIVERSITY OF ARKANSAS, Little Rock, AR (US)

(72) Inventor: Susanne Striegler, Fayetteville, AR (US)

(73) Assignee: Board of Trustees of the University of Arkansas, Little Rock, AR (US)

(*) Notice: Subject to any disclaimer, the term of this patent is extended or adjusted under 35 U.S.C. 154(b) by 0 days.

(21) Appl. No.: 15/451,478

(22) Filed: Mar. 7, 2017

(65) Prior Publication Data

US 2017/0275303 A1    Sep. 28, 2017

Related U.S. Application Data

(60) Provisional application No. 62/312,873, filed on Mar. 24, 2016.

(51) Int. Cl.

| | | |
|---|---|---|
| *C07F 1/08* | (2006.01) | |
| *B01J 31/22* | (2006.01) | |
| *C07H 3/02* | (2006.01) | |
| *C07H 1/00* | (2006.01) | |
| *C07F 1/00* | (2006.01) | |
| *C07C 215/44* | (2006.01) | |
| *C07C 211/36* | (2006.01) | |

(52) U.S. Cl.
CPC ....... *B01J 31/2239* (2013.01); *B01J 31/2243* (2013.01); *C07C 211/36* (2013.01); *C07C 215/44* (2013.01); *C07F 1/005* (2013.01); *C07H 1/00* (2013.01); *C07H 3/02* (2013.01); *B01J 2531/0208* (2013.01); *B01J 2531/0238* (2013.01); *B01J 2531/16* (2013.01); *C07B 2200/07* (2013.01); *C07C 2601/14* (2017.05)

(58) Field of Classification Search
None
See application file for complete search history.

(56) References Cited

FOREIGN PATENT DOCUMENTS

| | | |
|---|---|---|
| CN | 101239961 A | 8/2008 |
| CN | 102675264 A | 9/2012 |
| KR | 20040048621 A | 6/2004 |

OTHER PUBLICATIONS

Striegler et al. Journal of Catalysis, 338, 2016, 349-364 (Year: 2015).*

Investigations of Glycosylation Reactions with 2-N-Acetyl-2N,3O-oxazolidinone-Protected Glucosamine Donors; Olsson, Eriksson, Lahmann, and Oscarson; J. Org. Chem.; vol. 73; 2008; pp. 7181-7188.

Mild one-pot preparation of glycosyl bromides; Hunsen, Long, D'Ardenne, and Smith; Carbohydr. Res.; vol. 340; 2005; pp. 2670-2674.

Glycosylation chemistry promoted by iodine monobromide: Efficient synthesis of glycosyl bromides from thioglycosides, and O-glycosides from 'disarmed' thioglycosides and glycosyl bromides,; Kartha and Field; Tetrahedr. Letters; vol. 38, No. 47; 1997; pp. 8233-8236.

Programmable One-Pot Oligosaccharide Synthesis; Zhang, Ollmann, Ye, Wischnat, Baaspv, and Wong; Journal of the American Chemical Society; vol. 121; 1999; pp. 734-753.

Quantitative studies of the binding of the class II PapG adhesin from uropathogenic *Escherichia coli* to oligosaccharides; Larsson, Ohlsson, Dodson, Hultgren, Nilsson, and Kihlberg; Bioorg. Med. Chem.; vol. 11; 2003; pp. 2255-2261.

Hydrolysis of disaccharides over solid acid catalysts under green conditions; Marzo, Gervasini, and Carniti; Carbohydrate Research; vol. 347, Issue 1; Jan. 2012; pp. 23-31.

New symmetrical dinucleating ligand based assembly of bridged dicopper(II) and dizinc(II) centers: Synthesis, tructure, spectroscopy, magnetic properties and glycoside hydrolysis; Patra, Haldar, Kumar, Carrella, Ghosh, and Bera; Iorganic Chemica Acta; vol. 436; Sep. 2015; pp. 195-204.

An Efficient Stereoselective Dihydroxylation of Glycals using a Bimetallic System, RuCl3/CeCl3/NaIO4; Tiwari and Misra; Journal of Org. Chem.; vol. 71, Issue 7; 2006; pp. 2911-2913.

Artificial Metalloenzymes for Enantioselective Catalysis Based on Biotin-Avidin; Collot, Gradinaru, Humbert, Skander, Zocchi, and Ward; J.A.C.S.; vol. 125; 2003; pp. 9030-9031.

Four Orders of Magnitude Rate Increase in Artificial Enzyme-Catalyzed Aryl Glycoside Hydrolysis; Ortega-Caballero, Bjerre, Laustsen, and Bois; Journal of Org. Chem.; vol. 70; 2005; pp. 7217-7226.

Molecular Recognition of Carbohydrates with Artificial Receptors; Mazik, Cavga, and Jones; JACS, vol. 127, No. 25; Jun. 7, 2005; pp. 9045-9052.

(Continued)

*Primary Examiner* — Yun Qian
(74) *Attorney, Agent, or Firm* — Crowe & Dunlevy, P.C.

(57) ABSTRACT

Disclosed herein is a class of chiral binuclear metal complexes for stereoselective hydrolysis of saccharides and glycosides, and more particular chiral binuclear transition metal complex catalysts that discriminate epimeric glycosides and α- and β-glycosidic bonds of saccharides in aqueous solutions at near physiological pHs. The chiral binuclear metal complexes include a Schiff-base-type ligand derived from a chiral diamino building block, and a binuclear transition metal core, each which can be varied for selectivity. The metal core is a Lewis-acidic metal ion, such as copper, zinc, lanthanum, iron and nickel. The Schiff-base may be a reduced or non-reduced Schiff-base derived from aliphatic linear, aliphatic cyclic diamino alcohols or aromatic aldehydes. The ligand can be a penta- or heptadentate ligand derived from pyridinecarbaldehydes, benzaldehydes, linear or cyclic diamines or diamino alcohols.

2 Claims, 8 Drawing Sheets

(56) References Cited

OTHER PUBLICATIONS

Synthesis, Characterization, and Spectroscopic Investigation of New Iron(III) and Copper(II) Complexes of a Carboxylate Rich Ligand and Their Interaction with Carbohydrates in Aqueous Solution; Stewart, Arman, Bawazir, and Musie; Inorganic Chemistry; vol. 53; Jun. 13, 2014; pp. 10974-10988.

New Dinuclear Copper(II) and Zinc(III) Complexes for the Investigation of Sugar-Metal Ion Interactions; Bera and Patra; Carbohydrate Research; vol. 346, Issue 14; Oct. 11, 2011; pp. 2075-2083.

Synthesis, Structure, Spectroscopic Characterization, and Protein Binding Affinity of New Water-Soluble Herero- and Homometallic Tetranuclear [Cu"2Zn"2] and [Cu"4] Clusters; Patra, Sen, Ghorai, Musie, Mandal, Ghosh, and Bera; Inorganic Chemistry; vol. 52; Mar. 1, 2013; pp. 2880-2890.

Glycosylation Employing Bio-Systems: From Enzymes to Whole Cells; Kren and Thiem; Chemical Society Reviews; vol. 26; Jul. 4, 1997; pp. 463-473.

The Denaturation and Degradation of Stable Enzymes at High Temperatures; Daniel, Dines, and Petach; Biochemistry Journal; vol. 317; 1996; pp. 1-11.

Indigo Dye Production by Enzymatic Mimicking Based on an Iron(III)Porphyrin; Rebelo, Linhares; Simoes; Silva; Neves; Cavaleiro; and Freire; Journal of Catalysis; vol. 315; Jun. 2014; pp. 33-40.

Continuous Flow Catalysis with a Biomimetic Copper(II) Complex Covalently Immobilized on Graphite Felt; Marion, Muthusamy, and Geneste; Journal of Catalysis; vol. 286; Feb. 2012; pp. 266-272.

Structure and Catalytic Properties of Dimeric Copper(II) Acetato Complexes Encapsulated in Zeolite-Y; Chavan, Srinivas, and Ratnasamy; Journal of Catalysis; vol. 192; Feb. 2000; pp. 286-295.

Biomimetic Catalysis at Silicon Centre Using Molecularly Imprinted Polymers; Abbate, Bassindale, Brandstadt, and Taylor; Journal of Catalysis; vol. 284; Nov. 2011; pp. 68-76.

Study of Potential Binding of Biologically Important Sugars with a Dinuclear Cobalt(II) Complex; Bera and Patra; Carbohydrate Research; vol. 346; May 2011; pp. 733-738.

Discrimination of Epimeric Disaccharides by Templated Polymers; Striegler; Analytica Chimica Acta; vol. 539; Apr. 5, 2005; pp. 91-95.

Synthesis, crystal structure and investigation of mononuclear copper(II) and zinc(II) complexes of a new carboxylate rich tripodal ligand and their interaction with carbohydrates in alkaline aqueous solution; Stewart, Pedraza, Arman, Fan, Schilling, Szpoganicz, Musie; Journal of Inorganic Chemistry; vol. 149; Aug. 2015; pp. 25-38.

Binuclear Complexes for Aerobic Oxidation of Primary Alcohols and Carbohydrates; Striegler, Dunaway, Gichinga, and Milton; Tetrahedron; vol. 66; Oct. 2010; pp. 7927-7932.

A Sugar's Choice: Coordination to a Mononuclear or a Dinuclear Copper (II) Complex?; Striegler and Dittel; Inorganic Chemistry; col. 44; 2005; pp. 2728-2733.

A Sugar Discriminating Binuclear Copper(II) Complex; Striegler and Dittel; JACS; vol. 125; 2003; pp. 11518-11524.

Evaluating Binuclear Copper(II) Complexes for Glycoside Hydrolysis; Striegler, Dunaway, Gichinga, Barnett, and Nelson; Inorganic Chemistry; vol. 49; 2010; pp. 2639-2648.

Investigation of Sugar-Binding Sites in Ternary Ligand-Copper(II)-Carbohydrate Complexes; Striegler and Tewes; European Journal of Inorganic Chemistry; 2002; pp. 487-495.

Design of Biomimetic Catalysts by Molecular Imprinting in Synthetic Polymers: The Role of Transition State Stabilization; Wulff and Liu; Accounts of Chemical Research; vol. 45, No. 2; 2012; pp. 239-247.

Synthesis of the C-1-C-28 ABCD Unit of Spongistatin 1; Gaunt; Jessiman, Orsini; Tanner; Hook and Ley; Organic Letters; vol. 5, No. 25; 2003; pp. 4819-4822.

Synthesis and Highly Stereoselective Hydrogenation of the Statin Precursor Ethyl (5S)-5,6-Isopropylidenedioxy-3-oxohexanoate; Tararov, Konig, and Borner; Adv. Synth. Catal.; vol. 348; 2006; pp. 2633-2644.

Synthesis and SAR of Thrombin Inhibitors Incorporating a Novel 4-Amino-Morpholinone Scaffold: Analysis of X-ray Crystal Structure of Enzyme Inhibitor Complex; Nilsson, Kvarnstrom, Musil, Nilsson, and Samulesson; Journal of Medicinal Chemistry; vol. 46; 2003; pp. 3985-4001.

Versatile synthesis of stereospecifically labeled D-amino acids via labeled aziridines—preparation of (2R,3S)-[32H1]- and (2R,3R)-[2,3-2H2]-serine; (2S,2'S,3S,3'S)-[3,3'-2H2]- and (2S,2'S,3R,3'R)-[2,2',3,3'-2H4]-cystine; and (2S,3S)-[3-2H1-] and (2S,3R)-[2,3-2H2]-beta-chloroalanine; Axelsson, O'Toole, Spencer, and Young; J. Chem. Soc.; Perkin Trans. 1; 1994; pp. 807-815.

Configuration of 2-hydroxyputrescine; Kullnig, Rosano, Coulter, and Hurwitz; Journal of Biological Chemistry; vol. 248, No. 7; Apr. 1973; pp. 2487-2488.

Precise absolute-structure determination in light-atom crystals; Parsons and Flack; Acta Crystallogr. Sec. A60; 2004; p. s61.

Calculation of Equilibrium Constants from Multiwavelength Spectroscopic Data-IV, Model-Free Least-Squares Refinement by Use of Evolving Factor Analysis; Gampp, Maeder, Meyer, and Zuberbuhler; Talanta; vol. 33; 1986; pp. 943-951.

Crystal Structure, Solution Properties and Hydrolytic Activity of an Alkoxo-Bridged Dinuclear Copper(II) Complex, as a Ribonuclease Model; Gajda, Jancso, Mikkola, Lonnberg, and Sirges; J.A.C.S. Dalton Transactions; Issue 8; 2002; pp. 1757-1763.

Evaluation of the Carbohydrate Recognition Domain of the Bacterial Adhesin FimH: Design, Synthesis and Binding Properties of Mannoside Ligands; Sperling, Fuchs and Lindhorst; Organic & Biomolecular Chemistry; vol. 4; Dec. 2006; pp. 3913-3922.

Synthesis of Substituted Phenyl α-D-mannopyranosides; Vervoort and De Bruyne; Carbohydrate Research; 12; 1970; pp. 277-280.

Evaluating N-benzylgalactonoamidines as putative transition state analogs for b-galactoside hydrolysis; Fan, Striegler, Langston, and Barnett; Org. Biomol. Chem.; 12; May 2014; pp. 2792-2800.

Synthesis and evaluation of glycosyl donors with novel leaving groups for transglycosylations employing βgalactosidase from bovine testes; Kroger and Thiem; Carbohydrate Research; vol. 342; Oct. 2007; pp. 467-481.

Using simple donors to drive the equilibria of glycosyltransferase-catalyzed reactions; Gantt, Peltier-Pain, Cournoyer, and Thorson; Nature Chemical Biology, vol. 7; Aug. 2011; pp. 685-691.

Synthesis, characterization, kinetic parameters, and diagnostic application of a sensitive colorimetric substrate for β-galactosidase (2-chloro-4-nitrophenyl-β-D-galactopyranoside): Hwang and Scott; Bioorg. Chem.; vol. 21; 1993; pp. 284-293.

Stereoselective syntheses of O- and S-nitrophenyl glycosides. Part III. Syntheses in the α-D-galactopyranose and α-maltose series; Apparu, Blanc-Muesser, Defaye, and Driguez; Can. J. Chem.; vol. 59; 1981; pp. 314-320.

Lead Optimization Studies on FimH Antagonists: Discovery of Potent and Orally Bioavailable Ortho-Substituted Biphenyl Mannosides; Han, Pinkner, Ford, Chorell, Crowley, Cusumano, Campbell, Henderson, Hultgren, and Janetka; J. Med. Chem.; vol. 55; Mar. 2012; pp. 3945-3959.

Galactonoamidine derivatives with altered sugar moiety: synthesis and evaluation as inhibitors toward b-galactosidase (E. coli); Fan, Pickens, and Striegler; Biomol. Med. Chem.; vol. 24, Issue 4; Feb. 2016; pp. 661-671.

Selective Reduction of Azido Groups in Monosaccharides with Triphenyl-phosphine; Li, Fan, Zhang, and Ye; Synlett; No. 15; 2006; pp. 2464-2468.

Syntheses of p-nitrophenyl 3- and 4-thio-β-d-glycopyranosides; Chen and Withers; Carbohydr. Res.; vol. 345, Issue 18; Dec. 2010; pp. 2596-2604.

Carbohydrates as ligands: coordination equilibria and structure of the metal complexes; Gyurcsik arid Nagy; Coord. Chem. Rev.; vol. 203; 2000; pp. 81-149.

Catalytic proficiency: the unusual case of OMP decarboxylase; Miller and Wolfenden; Ann. Rev. Biochem.; vol. 71; 2002; pp. 847-885.

Synthesis of 2-hydroxymethyl-1-oxaquinolizidine; Borjesson and Welch; Tetrahedron; vol. 48, No. 30; 1992; pp. 6325-6334.

(56) References Cited

OTHER PUBLICATIONS

A convergent synthesis of the [4.4]-spiroacetal-γ-lactones cephalosporolides E and F; Brimble, Finch, Heapy, Fraser, Furkert, and O'Connor; Tetrahedron, vol. 67, Issue 5; Feb. 2011; pp. 995-1001.

A steroid hydroxylase inhibitor, diplodialide-A, and related metabolites from Diplodia pinea; Wada and Ishida; J. Chem. Soc.; Perkin Trans. 1; 1979; pp. 1154-1158.

Pheromone synthesis. XXIV. Synthesis of optically active forms of ipsdienol and ipsenol. The pheromone components of Ips bark beetles; Mori, Takigawa, and Matsuo; Tetrahedron; vol. 35; 1979; pp. 933-940.

A Method for Preparation of Unnatural (R)-Malic Acid Derivatives with Phenyisilanes; Cho, Song, and Jang; Synthetic Commun.; vol. 33, Issue 4; 2003; pp. 515-519.

Absolute configuration of (−)-hesperetin and (−)-liquiritigenin; Arakawa and Nakazaki Chemistry & Industry (London, United Kingdom); Jan. 1960; p. 73.

The absolute configurations of (=)-marmesin and (−)-hydroxytremetone; Harahda, Hirose, Nakazaki, and Uehara; Tetrahedron Letters; No. 9; 1968; pp. 5463-5466.

μ-Peroxo dicobalt complexes containing an unsymmetrical dinucleating ligand: synthesis, characterization, and oxygen affinity; Kayatani, Hayashi, Suzuki, and Uehara; Bulletin of the Chemical Society of Japan; vol. 67, No. 11; 1994; pp. 2980-2989.

2-Hydroxyputrescine amides as abnormal metabolites of wheat; Stoessl, Rohringer, and Samborski; Tetrahedron Letters; No. 33; 1969; pp. 2807-2810.

A short history of Shelx; Sheldrick; Acta Cryst; No. A64; 2008; pp. 112-122.

\* cited by examiner

CHIRAL BINUCLEAR METAL COMPLEXES FOR STEREOSELECTIVE HYDROLYSIS OF SACCHARIDES AND GLYCOSIDES

CROSS REFERENCE TO RELATED APPLICATIONS

This application claims priority to and the benefit of U.S. Provisional Patent Application Ser. No. 62/312,873, which is incorporated herein by reference in its entirety.

STATEMENT REGARDING FEDERALLY SPONSORED RESEARCH OR DEVELOPMENT

This invention was made with government support under Grant No. CHE-1305543, awarded by the National Science Foundation. The U.S. government has certain rights in the invention.

NAMES OF THE PARTIES TO A JOINT RESEARCH AGREEMENT

Not Applicable.

REFERENCE TO A SEQUENCE LISTING, A TABLE, OR A COMPUTER PROGRAM LISTING APPENDIX

Not Applicable.

STATEMENT REGARDING PRIOR DISCLOSURES BY THE INVENTOR OR A JOINT INVENTOR

Not Applicable.

BACKGROUND OF THE INVENTION

1. Field of the Invention

This invention relates generally to chiral binuclear transition metal complexes for stereoselective hydrolysis of saccharides and glycosides, and more particular to chiral binuclear Lewis acid transition metal catalysts that discriminate epimeric glycosides and $\alpha$- and $\beta$-glycosidic bonds of saccharides in aqueous solutions at near physiological pHs.

2. Description of the Related Art

Chiral discrimination is displayed by many enzyme classes, such as glycosidases, lipases, and esterases during bond formation and cleavage. While much progress has been made in the synthesis and evaluation of selective catalysts mimicking such features, most synthetic entities do not show sufficient diastereoselective or even chiral discrimination ability in aqueous solution. Man-made stereoselective catalysts for the discrimination of epimeric glycosides in aqueous solution or the selective hydrolysis of $\alpha$- and $\beta$-glycosidic bonds are not previously known.

A symmetric binuclear copper(II) complex, N,N'-{1,3-bis[(pyridine-2-ylmethyl)amino]propan-2-al}ato dicopper(II) ($\mu$-acetato) diperchlorate, was previously observed to interact differently with glycopyranosides upon binding in alkaline solution resulting in a 30-fold stronger binding to mannose over glucose. Similar observations were subsequently made using related metal complexes confirming the results of saccharide-metal complex binding in alkaline aqueous solution.

It is therefore desirable to provide chiral binuclear metal complexes for selective glycoside hydrolysis.

It is further desirable to provide chiral binuclear transition metal complexes for stereoselective hydrolysis of saccharides.

It is yet further desirable to provide asymmetrical binuclear Lewis acid transition metal complexes that discriminate epimeric saccharides during hydrolysis enabling chemoselective catalysis.

It is still yet further desirable to provide chiral binuclear Lewis acid transition metal complex catalysts that discriminate epimeric glycosides and aryl $\alpha$- and $\beta$-glycosidic bonds of saccharides in aqueous solutions at near physiological pHs It is still yet further desirable to provide chiral binuclear transition metal complex catalysts that at near neutral pH discriminate epimeric glycosides (e.g., $\alpha$-mannoside, $\alpha$-galactoside and $\alpha$-glucoside).

It is still yet further desirable to provide chiral binuclear transition metal complex catalysts that at near neutral pH discriminate disaccharides with different glycosidic bonds (e.g., maltose and cellobiose).

It is still yet further desirable to provide chiral binuclear transition metal complex catalysts that at near neutral pH discriminate epimeric disaccharides with identical glycosidic bonds (e.g., lactose and cellobiose).

It is still yet further desirable to provide chiral binuclear metal complexes that promote the development of catalysts to replace or complement slow-activating natural glycosidases.

It is still yet further desirable to provide chiral binuclear metal complexes that are advantageously easy to prepare including in large scale synthesis, easy to store at ambient temperatures, have unlimited shelf-life without a decrease in activity, superior stability against pH, temperature, solvents and/or aging, and insensitivity to poisoning by transition metal ion traces.

It is still yet further desirable to provide chiral binuclear Lewis acid transition metal complex catalysts to hydrolyze and/or digest glucosides, disaccharides and oligosaccharides selectively from industrial waste in food industry and/or from biomass.

Other advantages and features will be apparent from the following description, and from the claims.

SUMMARY OF THE INVENTION

In general, in a first aspect, the invention relates to a chiral binuclear transition metal complex for stereoselective hydrolysis of saccharides and glycosides. The chiral binuclear transition metal complex includes a Schiff-base ligand derived from a chiral diamino building block; and a binuclear transition metal core. The chiral diamino building block may be varied by changing the distance of the metals of the binuclear core in order to tune the complexes selectivity. The Schiff-base may be a reduced or non-reduced Schiff-base derived from aliphatic linear, aliphatic cyclic diamino alcohols or aromatic aldehydes. The complex is formulated to discriminate epimeric glycosides and α- and β-glycosidic bonds of saccharides in aqueous solutions at near physiological pHs. The metal core is a Lewis-acidic metal ion, such as copper, zinc, lanthanum, iron and nickel. The ligand can be a penta- or heptadentate ligand derived from pyridinecarbaldehydes, benzaldehydes, and linear or cyclic diamines or diamino alcohols, such as:

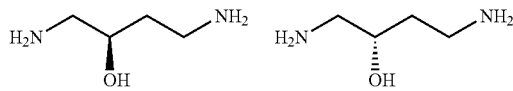

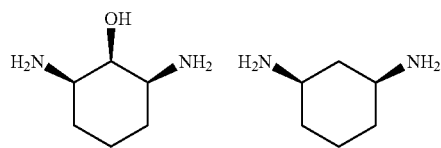

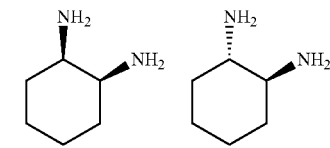

In general, in a second aspect, the invention relates to a chiral binuclear transition metal (II) complex having the formula $[M_2L_{-H}]^{3+}$, wherein L=S— or R—N,N'-1,3-bis[(pyridine-2-ylmethyl)amino]propan-2-al, wherein M is a Lewis-acidic metal ion selected from the group consisting of copper, zinc, lanthanum, iron and nickel. In particular, the complex may have the formula of $C_{19}H_{28}Cl_2Cu_2N_4O_{12}$, namely 2S, N, N'-[1,4-bis[(pyridin-2-ylmethyl)amino]butan-2-ol]ato dicopper(II) (μ-acetato) diperchlorate, 2R, N, N'-[1,4-bis[(pyridin-2-ylmethyl)amino]butan-2-ol]ato dicopper(II) (μ-acetato) diperchlorate or a combination thereof. Moreover, the complex can be:

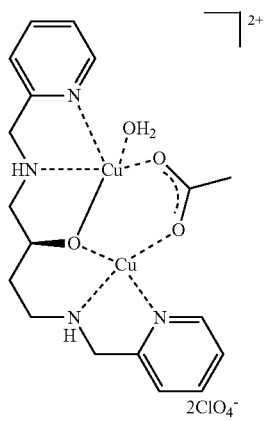

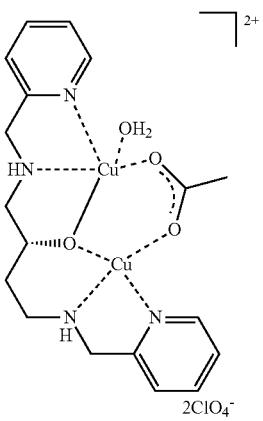

In general, in a third aspect, the invention relates to a method of hydrolysis of saccharides and glycosides. The method includes discriminating epimeric glycosides and α- and β-glycosidic bonds of saccharides in aqueous solutions at near physiological pHs using a chiral binuclear transition metal (II) complex. The S-2 enantiomer discriminates α-glycosidic bonds of the saccharides, and the R-2 enantiomer discriminates β-glycosidic bonds of the saccharides.

DETAILED DESCRIPTION OF THE INVENTION

Figure 1A:
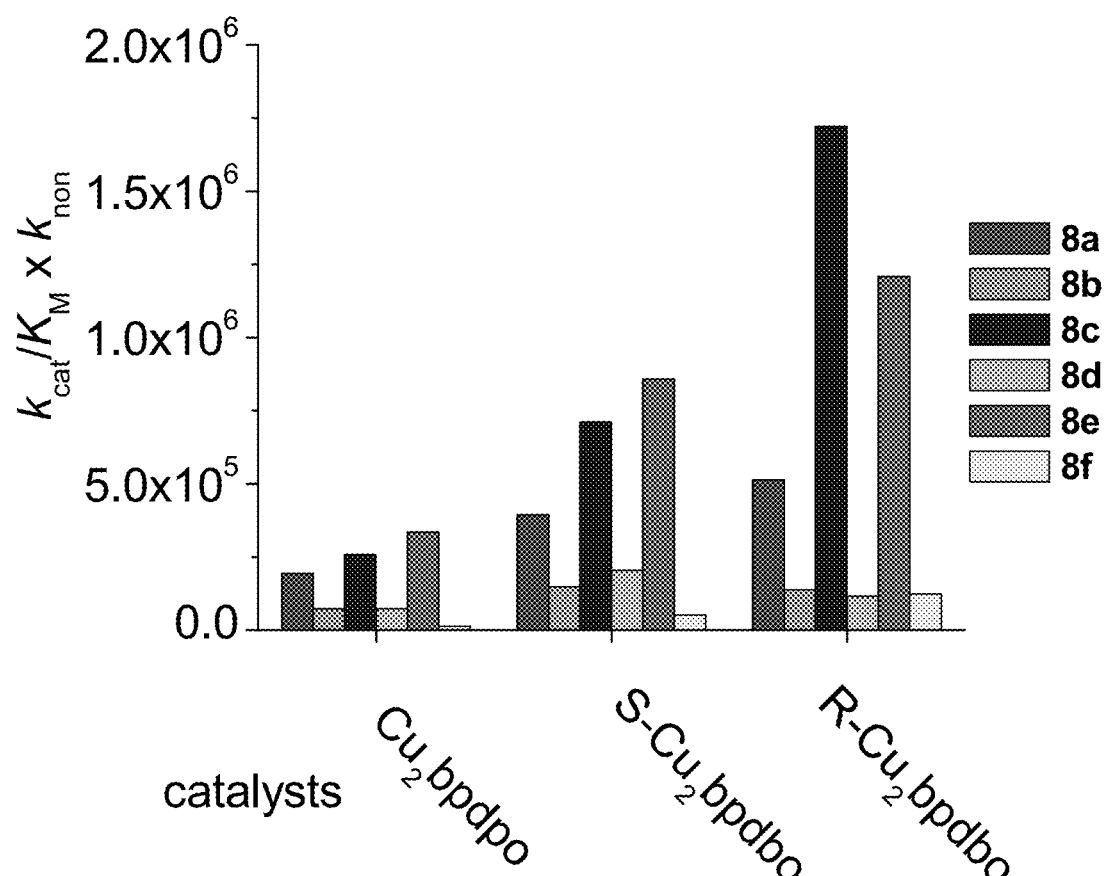
FIG. 1A graphically illustrates the catalytic proficiency of binuclear complexes 1, S-1 and R-1 in aqueous solution at pH 10.5 during the hydrolysis of 4-nitrophenylglycosides, and in particular graphically illustrates catalysts promoting the hydrolysis of glycosides as 8a-f.

The compounds and methods discussed herein are merely illustrative of specific manners in which to make and use this invention and are not to be interpreted as limiting in scope.

While the compounds and methods have been described with a certain degree of particularity, it is to be noted that many variations and modifications may be made in the details of the sequence, synthesis, components, concentrations and the arrangement of the processes and compositions without departing from the scope of this disclosure. It is understood that the compounds and methods are not limited to the embodiments set forth herein for purposes of exemplification.

The chiral binuclear metal complexes disclosed herein include a Schiff-base ligand derived from a chiral diamino building block, and a binuclear transition metal core, each which can all be varied. The chiral binuclear metal complexes may have formulas N, N'-[1,4-bis[(pyridin-2-ylmethyl)amino]butan-2-ol]ato dicopper(II) (μ-acetato) diperchlorate (racemic complex 2 below), 2S, N, N'[1,4-bis[(pyridin-2-ylmethyl)amino]butan-2-ol]ato dicopper(II) (μ-acetato) diperchlorate ("S-Cu$_2$bpdbo" or chiral complex S-2 below) and 2R, N, N'-[1,4-bis[(pyridin-2-ylmethyl)amino]butan-2-ol]ato dicopper(II) (μ-acetato) diperchlorate ("R-Cu$_2$bpdbo" or chiral complex R-2 below), as shown by the following structural formulas as:

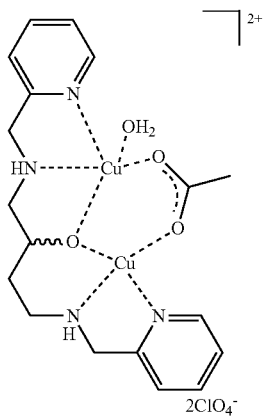

2

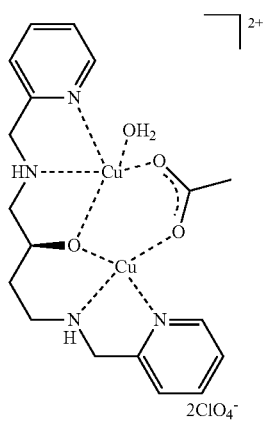

S-2

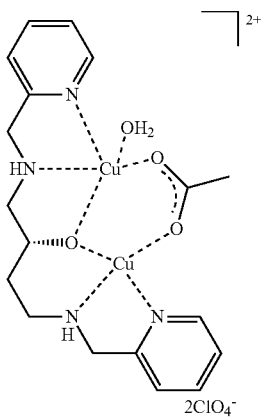

R-2

The chiral binuclear metal complexes can be synthesized from various Lewis acidic metals ions, such as $Zn^{2+}$, $La^{3+}$, $Fe^{3+}$, or $Ni^{2+}$, such as:

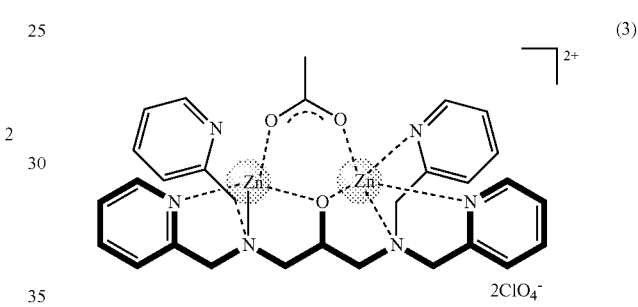

(3)

In addition, the chiral diamino building block can be varied by changing the distance of the metals of the binuclear core in order to tune the complexes selectivity. For example, the Schiff-base may be reduced or non-reduced and be derived from aliphatic linear, aliphatic cyclic diamino alcohols or aromatic aldehydes. The ligands can be penta- and heptadentates derived from pyridinecarbaldehydes, benzaldehydes, and linear or cyclic diamines and diamino alcohols, such as:

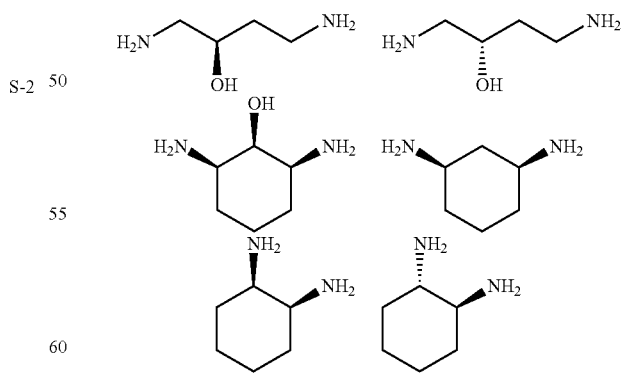

Examples

The chiral binuclear metal complexes disclosed herein are further illustrated by the following examples, which are provided for the purpose of demonstration rather than limitation. Although copper and zinc were used in the following examples due to their relatively low cost and high functionality, a number of other Lewis-acidic metals can be used.

As demonstrated by the following examples, chiral binuclear copper(II) and zinc (II) complexes S-1 and R-1 were synthesized and fully characterized including analysis by X-ray diffraction to confirm their stereochemistry. Subsequent evaluations of the complexes as catalysts for the cleavage of glycosidic bonds in aqueous alkaline solution showed moderate proficiency during the hydrolysis of 4-nitrophenyl glycosides and small discrimination ability among the selected epimeric substrates.

However, at near physiological pH, chiral complex S-1 shows distinct discrimination of epimeric aryl α-glycopyranosides. Discrimination of α- and β-glycosidic bonds in manno- and galactopyranosides by the same complex is apparent in their reaction rates, but masked in the catalytic proficiency by the different rates of the uncatalyzed reaction. By contrast, a 28-fold faster hydrolysis of aryl β- over α-glucopyranoside is noted translating into 3-fold higher proficiency of chiral complex S-1 for the hydrolysis of β-glucopyranoside, while the uncatalyzed reactions are of the same order of magnitude for both substrates. The discrimination is not related to the chirality of the complexes, but rather due to the configuration of the glycosides promoting cis- or trans-configured diol binding sites for catalyst coordination. Mechanistic studies reveal deprotonation of the hydroxyl group at C-2 as pre-requisite for catalysis.

An initial catalyst evaluation toward the hydrolysis of representative disaccharides revealed a preference of chiral complex S-1 for the cleavage of α-glycosidic bonds, and of chiral complex R-1 for the hydrolysis of β-glycosidic bonds. The chiral complexes S-1 and R-1 are catalysts able to discriminate epimeric and anomeric model glycosides promoting a stereoselective hydrolysis of glycosidic bonds in saccharides in aqueous solution at near neutral or physiological pH. The chiral catalysts S-1 and R-1 catalysts may be further developed for use with biomass transformation into valuable chemical synthons and fuels, applications in pharmaceutical industry, and/or the development of functional enzyme mimics.

Example 1—Synthesis of Chiral Binuclear Copper(II) Complexes

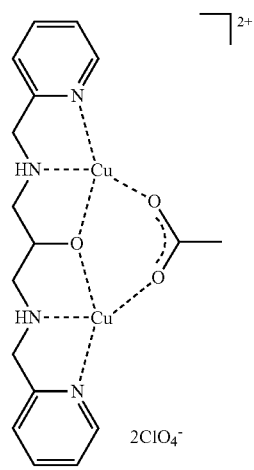

Symmetric complex N,N'-{1,3-bis[(pyridine-2-ylmethyl)amino]propan-2-al}ato dicopper(II) (μ-acetato) diperchlorate, ("Cu$_2$bpdpo") (symmetric complex 1 above) was derived from a reduced Schiff-base, free amino ligand, namely N,N'-1,3-bis[(pyridine-2-ylmethyl)amino]propan-2-al ("bpdpo") that was obtained from 1,3-diaminopropanol and pyridinecarbaldehyde.

Similarly, chiral complexes S-Cu$_2$bpdbo S-1 and R—Cu$_2$bpdbo R-1 were prepared according to Scheme 1 below by using enantiopure S- and R-malic acid 2 as inexpensive starting material for the synthesis of chiral 1,4-diaminobutanols 3. In short, the chiral S- and R-malic acid 4 were converted into methyl malates 5 using methanol in the presence of acetyl bromide. Treatment of esters 5 with excess ammonia in methanol yielded malamides 6. The hydrochlorides of S-3 and R-3 were obtained after reduction of malamides 6 with borane in THF and treatment of the reaction products with hydrogen chloride in absolute ethanol. Condensation of the free diaminoalcohols with pyridinecarbaldehyde afforded the chiral ligands S-bpdbo (S-7), and R-bpdbo (R-7), respectively, after reduction of the initially formed Schiff bases with sodium borohydride in methanol. Enantiopure binuclear copper(II) complexes S-1 and R-1 were prepared from the pentadentate ligands 7 and copper(II) acetate in methanol.

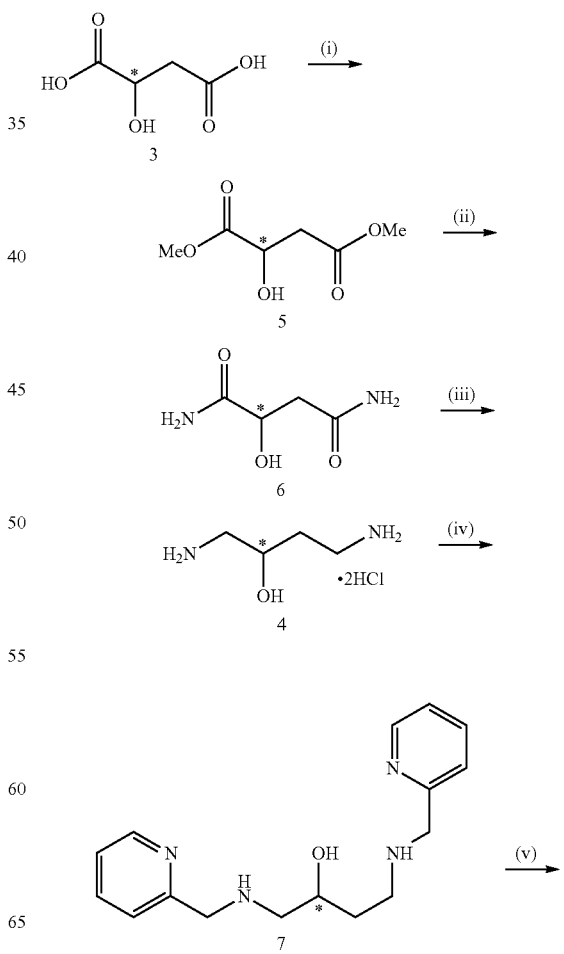

Scheme 1

-continued

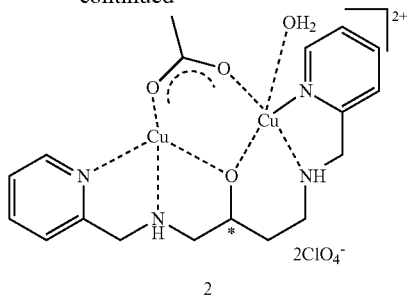

2

Acetyl bromide (2.2 mL, 0.031 mol) was added dropwise to 20 mL cold methanol. The solution was stirred for 30 minutes in ice. Then R-malic acid R-3, (12.5 g, 93.28 mmol) was added. The acid dissolved in about 5 min, and the resulting solution was stirred at ambient temperature. After 18 h, sodium bicarbonate (4.00 g, 0.048 mol) was added to the pale yellow solution. After 15 min of stirring, the mixture was filtered, the filtrate collected, and all volatile compounds evaporated in vacuum, yielding a sticky, oily raw material containing a white precipitate. The desired ester was distilled from this mixture in vacuum yielding 8.88 g of (R)-methyl malate (R-5) (54.77 mmol, 59%) of a colorless liquid.

The foregoing process was replicated using S-malic acid (S-3) in order to produce (S)-methyl malate (S-5).

(S)-methyl malate S-5 (6.20 g, 38.27 mmol) was then dissolved in 45 mL of 7 N ammonia in methanol under inert atmosphere and stirred at ambient temperature. After 24 h, the formed precipitate was separated by filtration and washed with methanol. The raw material was recrystallized from methanol and dried in vacuum yielding 2.20 g of (S)-malamide (S-6) (16.54 mmol, 43%) as a colorless solid.

(R)-malamide (R-6) was prepared from 6.84 g (42.22 mmol) of R-methyl malate R-5, as described for S-malamide from S-5, yielding 2.68 g (20.15 mmol, 48%) of R-6 as a colorless solid.

Under an inert atmosphere, 100 mL of 1 M borane in THF were added to ice-cooled S-6 (1.50 g, 11.28 mmol), and the resulting solution was heated to 77° C. After 11 h, the solution was cooled in an ice bath, and 40 mL of methanol were added in small portions to control the gas development. The solution was then heated to reflux for 1 h. After cooling, all volatile components were removed by rotary evaporation leaving the crude material as yellowish oil. The oil was dried in vacuum yielding a gummy-like off-white solid that was triturated with 200 mL water-free ethanol and filtered. The filtrate was subjected to gaseous HCl in the cold yielding a precipitate. The precipitate was isolated, washed once with 2 mL ice-cold ethanol and dried in vacuum over drierite yielding 0.575 g of (S)-1,4-diamino-2-butanol hydrochloride (S-4).

(R)-1,4-diamino-2-butanol hydrochloride (R-3) was obtained as colorless solid in 74% yield (5.96 g, 33.67 mmol) from 6.0 g (44.8 mmol) (R)-malamide R-6 as described above for the synthesis of S-3 from S-6.

Sodium hydroxide (1.53 g, 38.25 mmol) was added to a solution of S-4 (1.50 g, 8.475 mmol) in 80 mL methanol at ambient temperature. The initially turbid solution became clear and after 5 min turbid again. After 5 h, 2.27 g (21.19 mmol) of distilled 2-pyridinecarbaldehyde were added. After additional 22 h, the solution was diluted with 80 mL methanol prior to the addition of 3.04 g (0.080 mol) of sodium borohydride. After further 48 h, all volatile material was removed in vacuum to yield a residue that was taken up in 50 mL chloroform and 15 mL ice water. The organic layer was separated and extracted two times with 15 mL of ice water each. The combined organic layer was dried over sodium sulfate, filtered and concentrated to dryness yielding 2S, N, N'-bis(2-pyridylmethyl)-1,4-diaminobutan-2-ol, (S-bpdbo)(S-7) as a yellowish oil (1.42 g, 4.958 mmol, 59%). Typically, the S-7 ligand obtained by this procedure was diluted in an appropriate amount of ethanol to yield a 1 M stock solution, which was then used without further purification or characterization for the synthesis of copper (II) complexes. To obtain analytical data, 1.0 g (3.491 mmol) of the raw S-7 material were dissolved in dichloromethane and purified by column chromatography over silica gel (dichloromethane/methanol, 20/1-1/1, v/v) yielding 0.52 g (1.815 mmol, 52%) of S-7 as a pale yellowish oil.

2R, N, N'-bis(2-pyridylmethyl)-1,4-diaminobutan-2-ol, (R-bpdbo)(R-7) was prepared from R-6 using the same procedure as described for the synthesis of S-7 from S-6 above yielding 2.42 g (8.450, quantitative) of R-7 as raw material. Purification of the raw material by column chromatography over silica gel (dichloromethane/methanol, 20/1-1/1, v/v) yielded 2.01 g (7.0189 mmol, 83%) of R-7 as a pale yellowish oil.

Copper(II) acetate monohydrate (2.00 g, 10.00 mmol) were dissolved in 20 mL water and 400 mL methanol at ambient temperature. To the greenish-blue solution, 4.5 mL of the 1 M stock solution of S-7 in ethanol was added followed by a solution of 4.00 g (32.68 mmol) of sodium perchlorate in 10 mL water and 40 mL ethanol. The resulting dark blue solution was stirred for 12 h, filtered and concentrated below 50° C. to about 40 mL. Upon standing at ambient temperature, a precipitate formed that was isolated by filtration and dried at ambient temperature in air yielding 2.85 g (4.155 mmol) of a blue raw material. The raw material was recrystallized from aqueous methanol yielding 2.19 g (3.193 mmol, 32%) of 2S, N, N' [1,4-bis[(pyridin-2-ylmethyl)amino]butan-2-ol]ato dicopper(II) (µ-acetato) diperchlorate, ((S)-Cu$_2$bpdbo)(S-1) as a blue solid.

2R, N, N' [1,4-bis[(pyridin-2-ylmethyl)amino]butan-2-ol] ato dicopper(II) (µ-acetato) diperchlorate, (R-Cu$_2$bpdbo)(R-1), was prepared from 4.5 mL of a 1 M stock solution of R-77 as described for the preparation of S-Cu$_2$bpdbo from S-7 yielding 1.70 g (2.478 mmol, 25%) of R-1 as a blue solid.

Crystals of chiral complexes S-2 and R-2 were mounted on MiTeGen cryoloops in random orientations. Preliminary examination and data collection were performed using a Bruker X8 Kappa Apex II Charge Coupled Device (CCD) Detector system single crystal X-Ray diffractometer equipped with an Oxford Cryostream LT device. All data were collected using graphite monochromated Mo Kα radiation (λ=0.71073 Å) from a fine focus sealed tube X-Ray source. Preliminary unit cell constants were determined with a set of 36 narrow frame scans. Typical data sets consist of combinations of ω and φ scan frames with a scan width of 0.5° and counting time of 15 seconds/frame at a crystal to detector distance of 4.0 cm. The collected frames were integrated using an orientation matrix determined from the narrow frame scans. Apex II and SAINT software packages were used for data collection and data integration. [50] Analysis of the integrated data did not show any decay. Final cell constants were determined by global refinement of reflections harvested from the complete data set. Collected data were corrected for systematic errors using SADABS based on the Laue symmetry using equivalent reflections.

The disorder was modeled with partial occupancy atoms and geometrical restraints for both structures.

Structure solution and refinement were carried out using the SHELXTL-PLUS software package. The structures were solved by direct methods and refined successfully in the space group $P2_12_12_1$. Full matrix least-squares refinements were carried out by minimizing $\Sigma w(f_o^2-F_c^2)^2$. The non-hydrogen atoms were refined anisotropically to convergence. All hydrogen atoms were treated using appropriate riding models.

X-ray data for chiral complex S-2 ($C_{19}H_{28}O_2Cu_2N_4O_{12}$), blue needles (0.567×0.149×0.102 mm3, V 2640.4(3) Å3), were collected at 100 K. The crystals are orthorhombic, space group $P2_12_12_1$ with a=7.2680(5) Å, b=14.5809(10) Å and c=24.9155(17) Å, and Z=4. The θ-range for data collection was 1.618 to 30.743°. The number of reflections collected was 61147, with 8157 unique reflections ($R_{int}$=0.0402). Refinement by full-matrix least-squares on $F^2$, 392 parameters, gave final R indices (I>2σ$_1$) $R_1$=0.0290, weighted $R_2$=0.0706; R indices on all data were $R_1$=0.0335 and weighted $R_2$=0.0721. The absolute structure parameter x was −0.020(3); CCDC 1431768.

X-ray data for chiral complex R-2 ($C_{19}H_{28}Cl_2Cu_2N_4O_{12}$), blue needles (0.516×0.104×0.066 mm3, V 2650.10(13) Å3), were collected at 100 K. The crystals are orthorhombic, space group $P2_12_12_1$ with a=7.2854(2) Å, b=14.5841(4) Å and c=24.9419(7) Å, and Z=4. The θ-range for data collection was 1.633 to 34.970°. The number of reflections collected was 88769, with 11457 unique reflections ($R_{int}$=0.0662). Refinement by full-matrix least-squares on $F^2$, 385 parameters, gave final R indices (I>2σ$_1$) $R_1$=0.0398, weighted $R_2$=0.0832; R indices on all data were $R_1$=0.0570 and weighted $R_2$=0.0891. The absolute structure parameter x was −0.021(5); CCDC 1431767.

Example 2—Characterization of Chiral Binuclear Copper(II) Complexes in Solution

To evaluate the chiral binuclear metal complexes for their ability to discriminate glycosidic bonds, two pH values for kinetic evaluations were selected reflecting different complex compositions. The composition of chiral complexes S-1 and R-1 in aqueous solution is identical to the speciation of racemic complex 1 and deduced from data previously determined using spectrophotometric titration methods. At pH 10.5, the predominant species of chiral complexes S-1 and R-1 is still a $[Cu_2L_{-H}]^{3+}$ species (57.5%), while only one other additional $[Cu_2L_{-H}(OH)]^{2+}$ species (42.5%) is formed (L=S- and R-bpdbo, respectively) (Scheme 2 below, X=H$_2$O). By contrast, symmetric complex 1 forms under these conditions $[Cu_2L_{-H}(OH)_2]^+$ as the main species (88.5%) in equilibrium with a minor $[Cu_2L_{-H}(OH)]^{2+}$ species (11.5%). Mononuclear complexes formed from remaining ligand or free metal ions can be neglected for catalysis under the applied conditions or were demonstrated to be inactive. At pH 7.5, chiral complexes S-1 and R-1 exist predominantly as a binuclear $[Cu_2L_{-H}]^{3+}$ species (94%, L=S- and R-bpdbo, respectively), while symmetric complex 1 exists as $[Cu_2L_{-H}(OH)]^{2+}$ species (98.6%, L=bpdpo) (Scheme 3, X=H$_2$O).

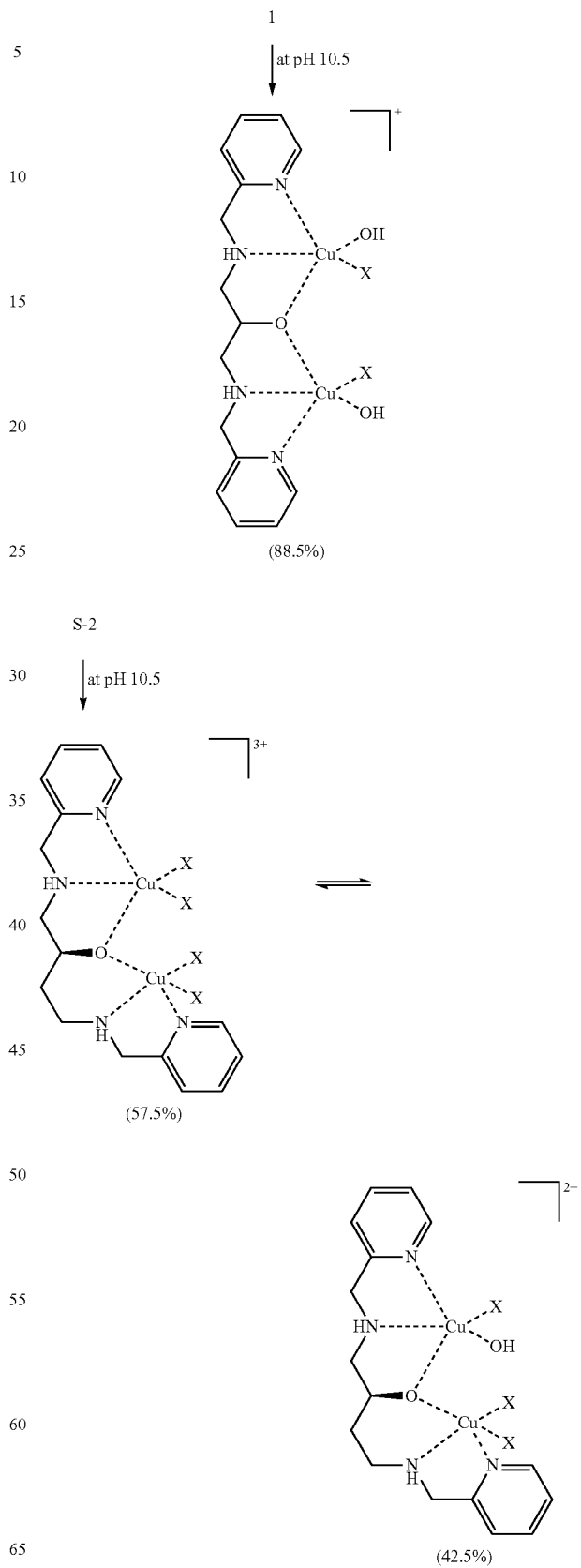

Scheme 2

Scheme 3

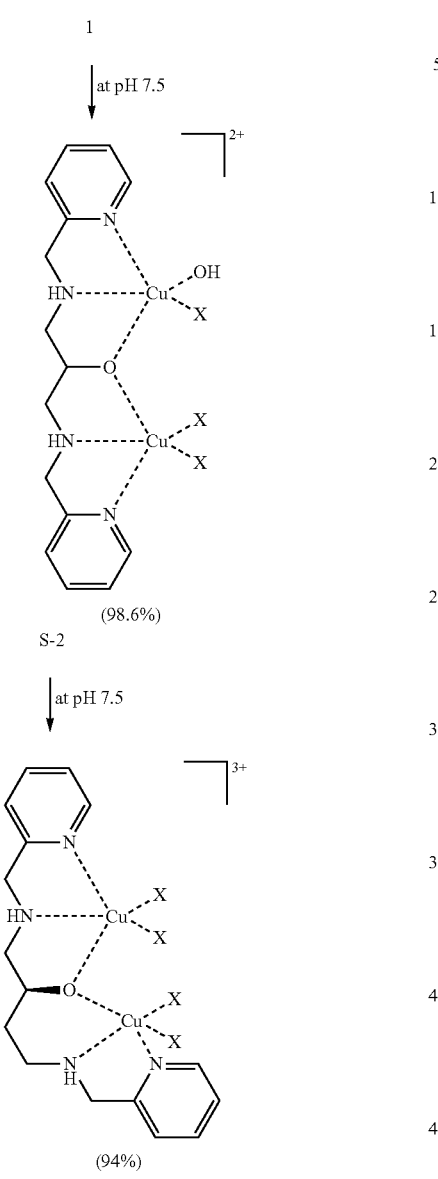

To allow a comparison between all complexes and species derived therefrom during the hydrolysis of glycosidic bonds, the catalyst amounts used for the determination of kinetic parameters are corrected to reflect the different amounts of the respective catalytically active species.

Example 3—Differentiation of 4-Nitrophenyl Glycosides During Catalytic Hydrolysis in Alkaline Solution Based on previously established assays using UV/Vis spectroscopy to evaluate the catalytic activity of symmetric complex 1 and racemic complex 2 during glycoside hydrolysis, chiral catalysts S-1 and R-1 were extended and the substrate scope by employing six commercially available 4-nitrophenylglycosides, and transferred the previous assay from 1 mL standard cuvettes into 96-well plate format. The adjusted procedure allows considerably faster catalyst screening using smaller compound amounts and volumes, and thereby circumvents previously observed limitations caused by low substrate solubility.

Along these lines, the catalytic hydrolysis of 4-nitrophenyl-α-D-mannopyranoside (8a), 4-nitrophenyl-β-D-mannopyranoside (8b), 4-nitrophenyl-α-D-galactopyranoside (8c), 4-nitrophenyl-β-D-galactopyranoside (8d), 4-nitrophenyl-α-D-glucopyranoside (8e), and 4-nitrophenyl-β-D-glucopyranoside (8f), whose structural formulas are shown below, was studied by UV/Vis spectroscopy recording the product formation at 405 nm over time pursuant to Scheme 4.

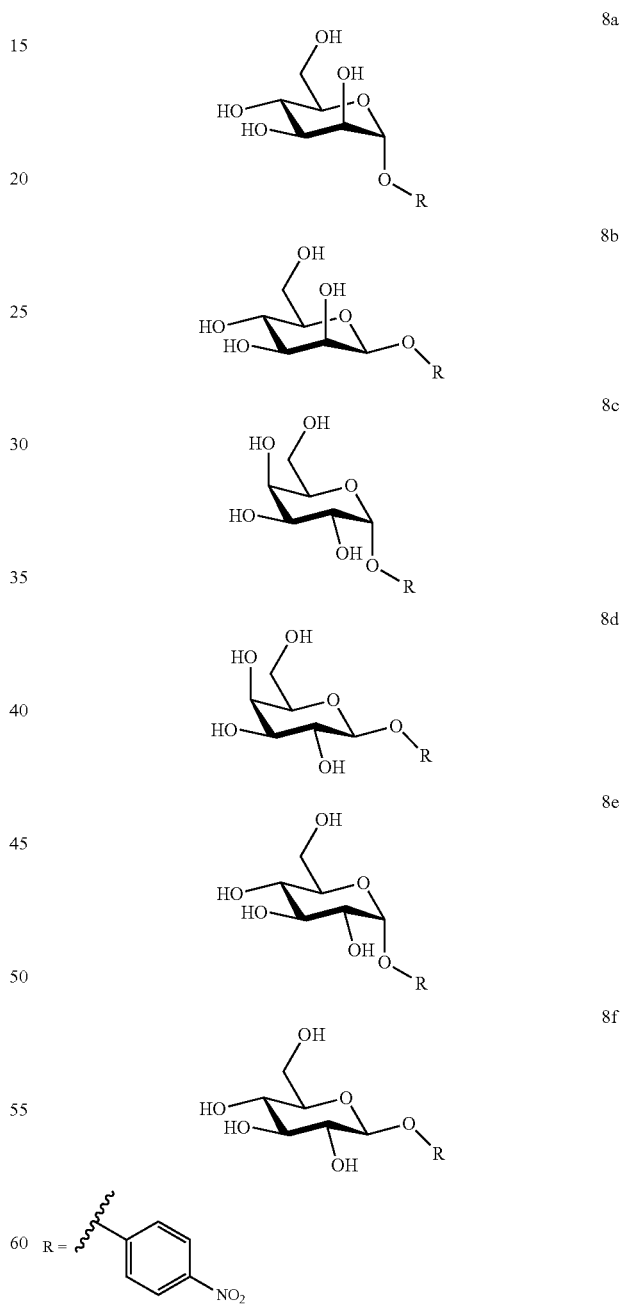

Catalytic hydrolysis of 8e is illustrated in Scheme 4 below as representative example for the hydrolysis of substrates 8a-f Scheme 4

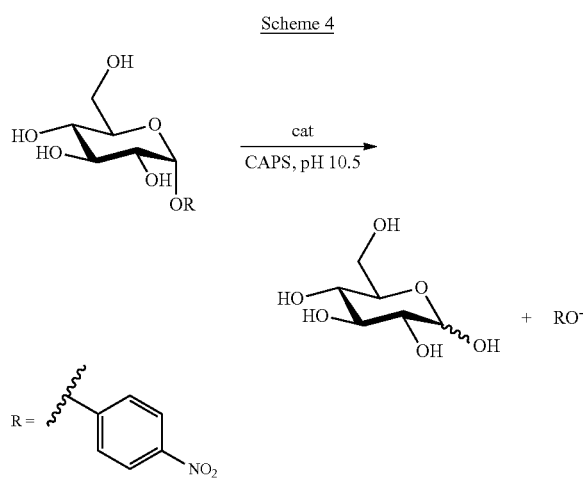

The adjusted assay has a total volume of 200 μL and lowered the catalyst concentration from 0.1 mM to 0.03 mM, while the substrates were used between 6-10 mM. The substrate hydrolysis depends linearly on the catalyst concentration under these conditions. The measured absorbance was converted into concentration using the apparent extinction coefficient $\varepsilon_{app}$, corrected for the catalyst concentration, its relative speciation amount, and the uncatalyzed reaction, and then plotted versus the substrate concentration. By applying a non-linear fit to the resulting hyperbolic data, the catalytic rate constant $k_{cat}$ [min$^{-1}$] and the substrate affinity $K_M$ [mM] were determined utilizing the Michaelis-Menten model (Table 1).

TABLE 1

Kinetic parameters for the hydrolysis of 4-nitrophenylglycosides 8a-f at pH 10.5 and 30° C.

| Entry | S | cat | $k_{cat} \times 10^{-3}$ [min$^{-1}$] | $K_M$ [mM] | $k_{cat}/K_M \times 10^{-3}$ [min$^{-1}$ M$^{-1}$] | $k_{cat}/k_{non} \times 10^3$ [M] | $k_{cat}/(K_M \times k_{non})$ |
|---|---|---|---|---|---|---|---|
| 1 | 8a | 1 | 3.09 | 107.5 | 28.7 | 20.7 | 193,000 |
| 2 | | S-1 | 6.32 | 107.7 | 58.7 | 42.4 | 394,000 |
| 3 | | R-1 | 4.42 | 57.7 | 76.6 | 29.7 | 514,000 |
| 4 | 8b | 1 | 0.30 | 21.0 | 14.3 | 1.5 | 74,000 |
| 5 | | S-1 | 0.76 | 26.6 | 28.6 | 3.9 | 147,000 |
| 6 | | R-1 | 0.64 | 23.9 | 26.7 | 3.3 | 138,000 |
| 7 | 8c | 1 | 0.65 | 70.5 | 9.2 | 18.2 | 258,000 |
| 8 | | S-1 | 1.07 | 42.1 | 25.4 | 29.9 | 710,000 |
| 9 | | R-1 | 1.15 | 18.7 | 61.7 | 32.1 | 1,720,000 |
| 10 | 8d | 1 | 0.12 | 12.1 | 9.9 | 0.9 | 74,000 |
| 11 | | S-1 | 0.28 | 10.2 | 27.5 | 2.1 | 206,000 |
| 12 | | R-1 | 0.26 | 16.8 | 15.5 | 1.9 | 116,000 |
| 13 | 8e | 1 | 0.27 | 7.5 | 35.8 | 2.5 | 335,000 |
| 14 | | S-1 | 0.83 | 9.1 | 91.5 | 7.8 | 857,000 |
| 15 | | R-1 | 0.81 | 6.3 | 129.0 | 7.6 | 1,210,000 |
| 16 | 8f | 1 | 0.15 | 53.2 | 2.8 | 0.3 | 13,000 |
| 17 | | S-1 | 0.81 | 72.2 | 11.2 | 1.4 | 51,000 |
| 18 | | R-1 | 1.17 | 42.8 | 27.3 | 20.0 | 124,000 | where $k_{non}$ 8a = 1.5 × 10$^{-7}$ [min$^{-1}$ M$^{-1}$], $k_{non}$ 8b = 1.9 × 10$^{-7}$ [min$^{-1}$ M$^{-1}$], $k_{non}$ 8c = 0.4 × 10$^{-7}$ [min$^{-1}$ M$^{-1}$], $k_{non}$ 8d = 1.3 × 10$^{-7}$ [min$^{-1}$ M$^{-1}$]; $k_{non}$ 8e = 1.1 × 10$^{-7}$ [min$^{-1}$ M$^{-1}$], $k_{non}$ 8f = 2.2 × 10$^{-7}$ [min$^{-1}$ M$^{-1}$]

The uncatalyzed reactions ($k_{non}$) of all substrates remain in the same order of magnitude as previously determined ($k_{non}$=0.4–2.2×10$^{-7}$ min$^{-1}$ M$^{-1}$). For comparison of different substrates, only the proficiency ($k_{cat}/(K_M \times k_{non})$) of the catalysts is discussed to account for the different strengths of glycosidic bonds and the resulting different hydrolysis rates in absence and presence of catalysts.

Figure 1B:
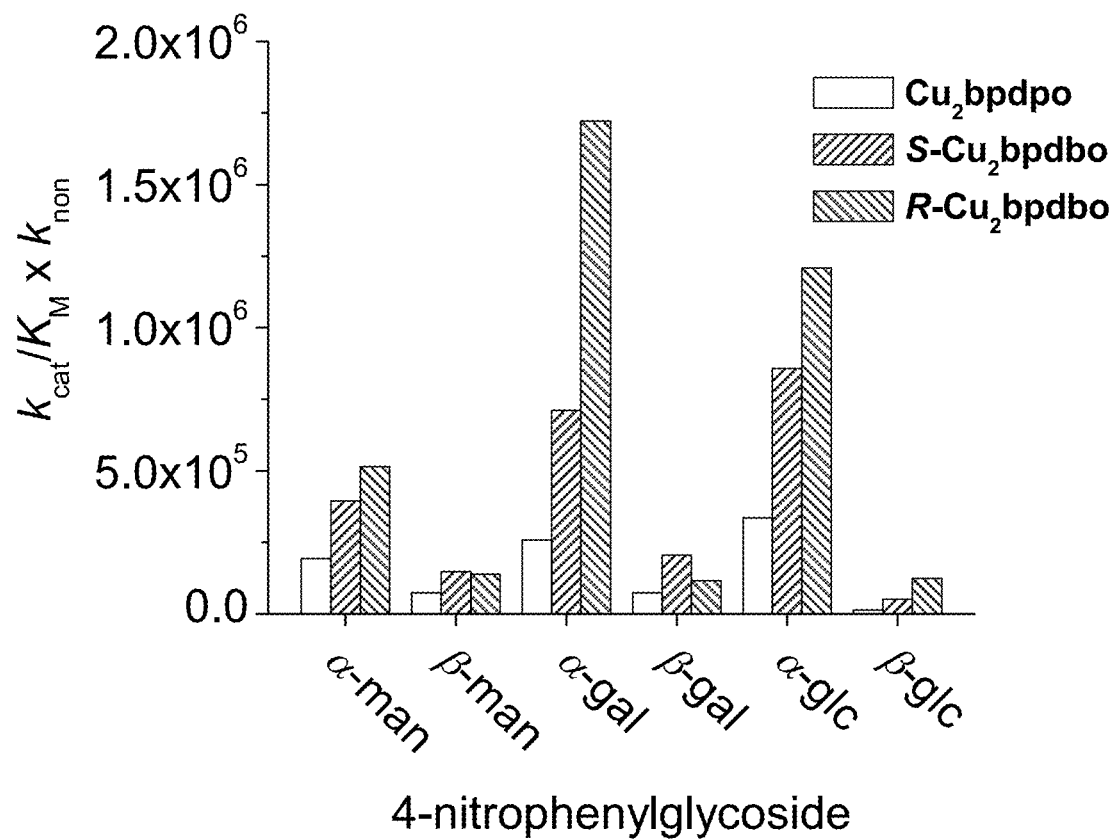
FIG. 1B graphically illustrates the catalytic proficiency of binuclear complexes 1, S-1 and R-1 in aqueous solution at pH 10.5 during the hydrolysis of 4-nitrophenylglycosides, and in particular graphically illustrates glycosides 8a-f hydrolyzed by catalysts 1, S-1 and R-1.

The catalytic proficiency of the symmetric complex 1 under the employed conditions is very modest and shows only limited differentiation of substrates with α-glycosidic bond (8a, 8c and 8e) from substrates with β-glycosidic bond (8b, 8d and 8f) that are typically hydrolyzed even less efficiently, if at all (FIG. 1). The substrates are not significantly discriminated by symmetric complex 1 for their epimeric sugar moiety.

By contrast, both chiral complexes S-1 and R-1 are more proficient for cleaving the glycosides 8a-f than symmetric complex 1 (FIG. 1A). In addition, chiral complexes S-1 and R-1 show higher proficiency than symmetric complex 1 to hydrolyze α- over β-glycosidic bonds. Chiral complex R-1 hydrolyzes 8c with a 6.7-fold, and 8e with a 3.6-fold higher proficiency than symmetric complex 1, and shows a 1.3-fold, and 2.4-fold, respectively, higher proficiency for the hydrolysis of the same substrates than chiral complex S-1. While chiral complex R-1 shows the overall highest proficiency for hydrolyzing 4-nitrophenyl-α-D-galactopyranoside (8c) ($k_{cat}/K_M \times k_{non}$=1,720,000), the same complex shows an almost 10-fold higher proficiency for hydrolyzing the β-glucosidic bond in 8f (R-1: $k_{cat}/K_M \times k_{non}$=124,000) than symmetric complex 1 $k_{cat}/K_M \times k_{non}$=12,800).

While the results encourage further investigation of binuclear Cu(II) complexes S-1 and R-1 for their ability to discriminate glycosidic bonds in natural systems, including disaccharides, initial attempts to use these substrates under the above described assay conditions were futile and led to catalyst destruction. Visibly to the naked eye, the originally blue solutions will turn green and then orange within 1-2 h indicating the formation of Cu(I) oxide without evidence for a significant hydrolysis of the disaccharide at 30 or 40° C. Decreasing the pH of the solution to pH 7 or 8 was found to increase catalyst stability, but resulted in catalyst inactivation below 40° C. (see below). Selective oxidation of the primary hydroxyl group at C-6 in methyl glycosides was previously observed for symmetric complex 1 after activation with TEMPO in alkaline solution.

Following the hydrolysis of glycosides and natural saccharides at near physiological pH appears more relevant for the synthesis of functional enzyme models and modelling of enzyme activity. Unfortunately, the commercially available 4-nitrophenyl glycopyranosides have a low molar extinction coefficient under these conditions that hamper their use as model compounds at pH values below 9. As a consequence, rapid catalyst screening in 96-well plate format using such substrates is limited and results in high uncertainty for the evaluation of the catalyst performance due to the resulting small apparent absorbance changes, small extinction coefficients, and large errors of the associated data. To overcome this obstacle, at least two approaches may be utilized: the use of derivatized nitrophenyl glycosides with large extinction coefficients suitable to follow hydrolysis reactions at near physiological pH by UV/Vis spectroscopy, and/or the use of 'real' saccharides instead of phenylglycoside model compounds after further modification of the current assay. Toward the development of functional enzyme models, both approaches were followed and the results are summarized below.

Example 4—Discrimination of 2'-Chloro-4'-Nitrophenyl Glycopyranosides During Catalytic Hydrolysis at Physiological pH With substrates 9a-i on hand, their hydrolysis was initially studied under the same conditions as outlined above for the hydrolysis of p-nitrophenyl glycopyranosides, i.e. at alkaline pH. While the catalytic rate constants are of similar order of magnitude, the uncatalyzed hydrolyses of 2'-chloro-4'-nitrophenyl glycopyranosides (e.g. $k_{non}$=0.5-3.3×10$^{-4}$ [min$^{-1}$ M$^{-1}$], 50 mM CAPS buffer, pH 10.5, 30° C.) are considerably faster than the uncatalyzed hydrolysis reactions of p-nitrophenyl glycopyranosides (Table 1) rendering all complexes less efficient as catalysts and the differences in catalyst proficiency smaller. This observation accounts for the decreased stability of the glycosidic bond after introduction of the chloro-substituent in the ortho position of the aglycon. However, the decreased stability of the glycosidic bond in the 2'-chloro-4'-nitrophenyl glycopyranosides does allow the investigation of the catalyst performance at near neutral pH values as noted above.

Along these lines, the proficiency of the selected complexes toward glycoside hydrolysis was evaluated in 50 mM HEPES buffer at pH 7.50 and 30° C. Typically, lag times around 200 min were observed prior to the start of the catalytic hydrolyses that may indicate substrate deprotonation, distortion or inversion of the glycon upon interaction with the catalyst. Data collection over 9-12 h allowed the determination of all kinetic parameters after conversion of the observed absorbance data into product concentrations and application of the Michaelis-Menten model (Table 2).

TABLE 2

Kinetic parameters for the catalytic hydrolysis of 9a-f, i at pH 7.5 and 30° C.

| Entry | S | cat | $k_{cat}$ × 10$^{-3}$ [min$^{-1}$] | $K_M$ [mM] | $k_{cat}/(K_M × k_{non})$ |
|---|---|---|---|---|---|
| 1 | 9a | 1 | 1.51 | 25.7 | 43,000 |
| 2 | | S-1 | 1.74 | 30.0 | 42,000 |
| 3 | | R-1 | 1.98 | 38.3 | 38,000 |
| 4 | 9b | 1 | 0.42 | 25.6 | 62,000 |
| 5 | | S-1 | 0.33 | 22.8 | 55,000 |
| 6 | | R-1 | 0.26 | 17.3 | 57,000 |
| 7 | 9c | 1 | 0.37 | 15.6 | 51,000 |
| 8 | | S-1 | 0.28 | 8.8 | 68,000 |
| 9 | | R-1 | 0.71 | 31.6 | 48,000 |
| 10 | 9d | 1 | 5.49 | 73.0 | 35,400 |
| 11 | | S-1 | 4.55 | 58.4 | 37,000 |
| 12 | | R-1 | 3.28 | 43.2 | 36,000 |
| 13 | 9e | 1 | 0.07 | 4.5 | 66,000 |
| 14 | | S-1 | 0.06 | 2.1 | 121,000 |
| 15 | | R-1 | 0.06 | 2.2 | 118,000 |
| 16 | 9f | 1 | 1.10 | 30.7 | 50,000 |
| 17 | | S-1 | 1.67 | 47.7 | 49,000 |
| 18 | | R-1 | 1.26 | 45.0 | 39,000 |
| 19 | 9i | 1 | 0.53 | 4.0 | 60,000 |
| 20 | | S-1 | 0.49 | 4.8 | 47,000 |
| 21 | | R-1 | 0.24 | 1.9 | 58,000 | where $k_{non}$ 9a = 1.3 × 10$^{-6}$ [min$^{-1}$ M$^{-1}$]; $k_{non}$ 9b = 2.6 × 10$^{-7}$ [min$^{-1}$ M$^{-1}$]; $k_{non}$ 9c = 6.7 × 10$^{-7}$ [min$^{-1}$ M$^{-1}$]; $k_{non}$ 9d = 2.1 × 10$^{-6}$ [min$^{-1}$ M$^{-1}$]; $k_{non}$ 9e = 2.4 × 10$^{-7}$ [min$^{-1}$ M$^{-1}$]; $k_{non}$ 9f = 7.1 × 10$^{-7}$ [min$^{-1}$ M$^{-1}$]; $k_{non}$ 9i = 2.2 × 10$^{-6}$ [min$^{-1}$ M$^{-1}$]

Figure 2:
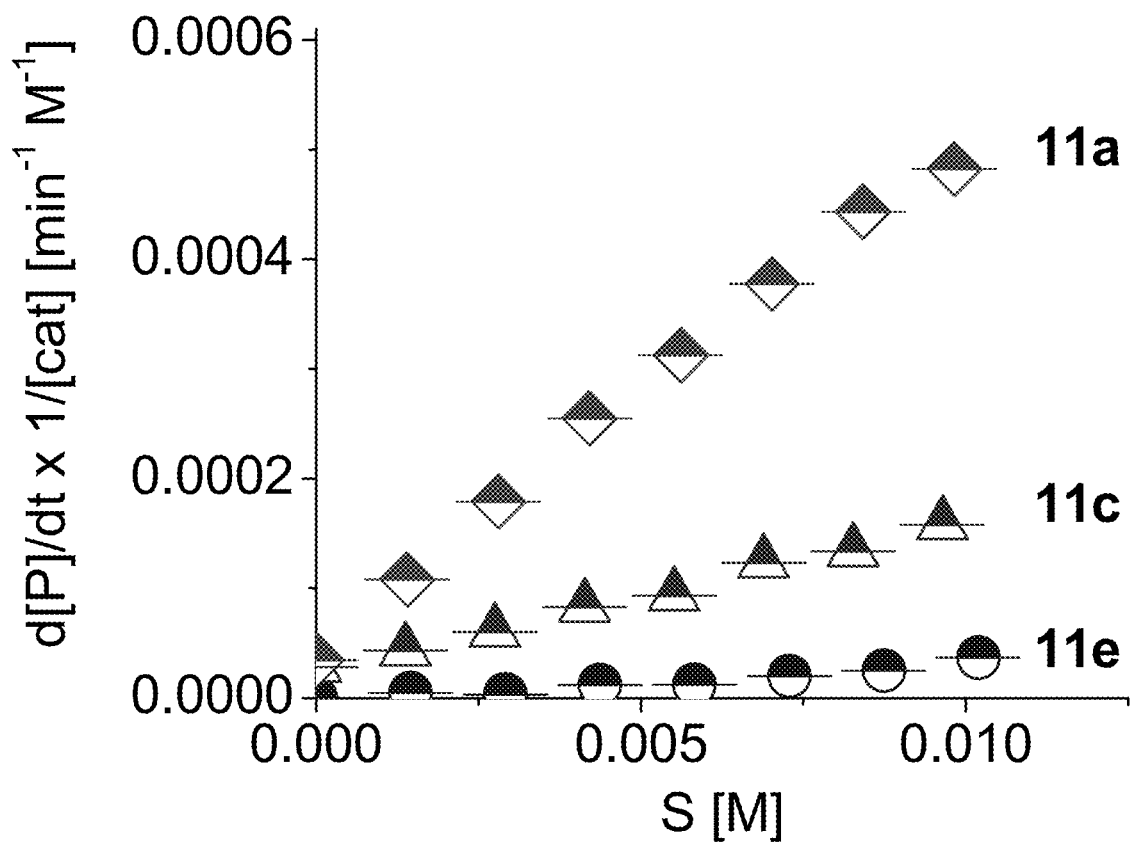
FIG. 2 graphically illustrates the product formation over time, catalyst and substrate concentration for the hydrolysis of 9a, 9c, and 9e by S-1 in 50 mM HEPES buffer at 7.50±0.05 and 30.0±0.1° C.
Figure 3:
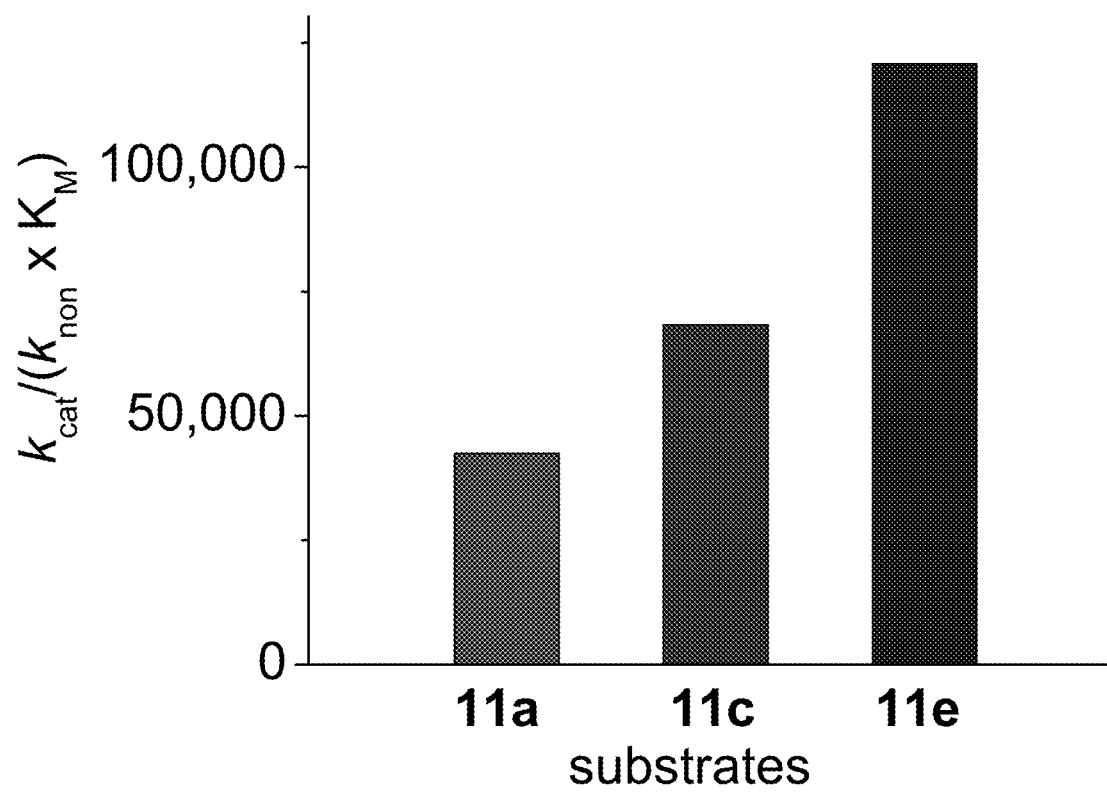
FIG. 3 graphically illustrates the proficiency of S-1 for the catalytic hydrolysis of α-glycosides 9a, 9c, and 9e in 50 mM HEPES buffer at pH 7.50±0.05 and 30.0±0.1° C.

Example 5—Performance of S-1 During Hydrolysis of Epimeric α-Glycopyranosides Chiral catalyst S-1 discriminates epimeric α-glycosides 9a, 9c and 9e by catalyzing their hydrolysis with significantly different rates (FIG. 2). The rate for the catalyzed hydrolysis of 9a is more than 6-fold higher than for 9c and 29-fold higher than for 9e pointing at a significant influence of the hydroxyl groups at C-2 and C-3 in the glycon of the substrates during metal complex-catalyzed hydrolysis. Substrates with hydroxyl groups trans to each other (9c, 9e) promote slower hydrolysis than a substrate with hydroxyl groups cis to each other (9a). This observation correlates with known metal complex coordination abilities to trans-diols (weak) and cis-diols (strong) in pyranosides. To account for uncatalyzed background reactions and different substrate affinity toward a complex, the catalyst proficiency ($k_{cat}/K_M × k_{non}$) was calculated (FIG. 3).

The known lability of the α-glycosidic bond in 9a causes its uncatalyzed hydrolysis ($k_{non}$) to be about an order of magnitude faster than for 9c and 9e. Thus, the catalytic proficiency of chiral complex S-1 decreases in the order of 9e>9c>9a showing a distinct discrimination of epimeric glycosides by a metal complex at near neutral pH. For comparison, symmetric complex 1 shows an overall lower proficiency to hydrolyze the epimeric substrates with negligible differences (1.5-fold or less).

Example 6—Performance of S-1 During Hydrolysis of α- and β-Glycopyranosides

The rate of the chiral complex S-1 catalyzed hydrolysis of α-mannoside 9a is about 5-fold higher than for β-mannoside 9b, while the reverse trend is observed for gluco- and galactosides where the β-glycosides are hydrolyzed 16-fold (9d) and 28-fold (9f) faster than their corresponding α-glycosides (Table 2, entries 2 & 5; 8 & 11; 14 & 17). As the uncatalyzed hydrolyses of the manno- and galactosides differ by an order of magnitude within each α-/β-pyranoside pair (Table 2, footnote), the catalytic proficiency of the catalyst for the hydrolysis of the respective α- and β-glycosides do not reflect the discrimination its ability, but reveal a rather equivalent catalytic proficiency near 50,000 instead. Substrate 9i behaves likewise.

Figure 4:
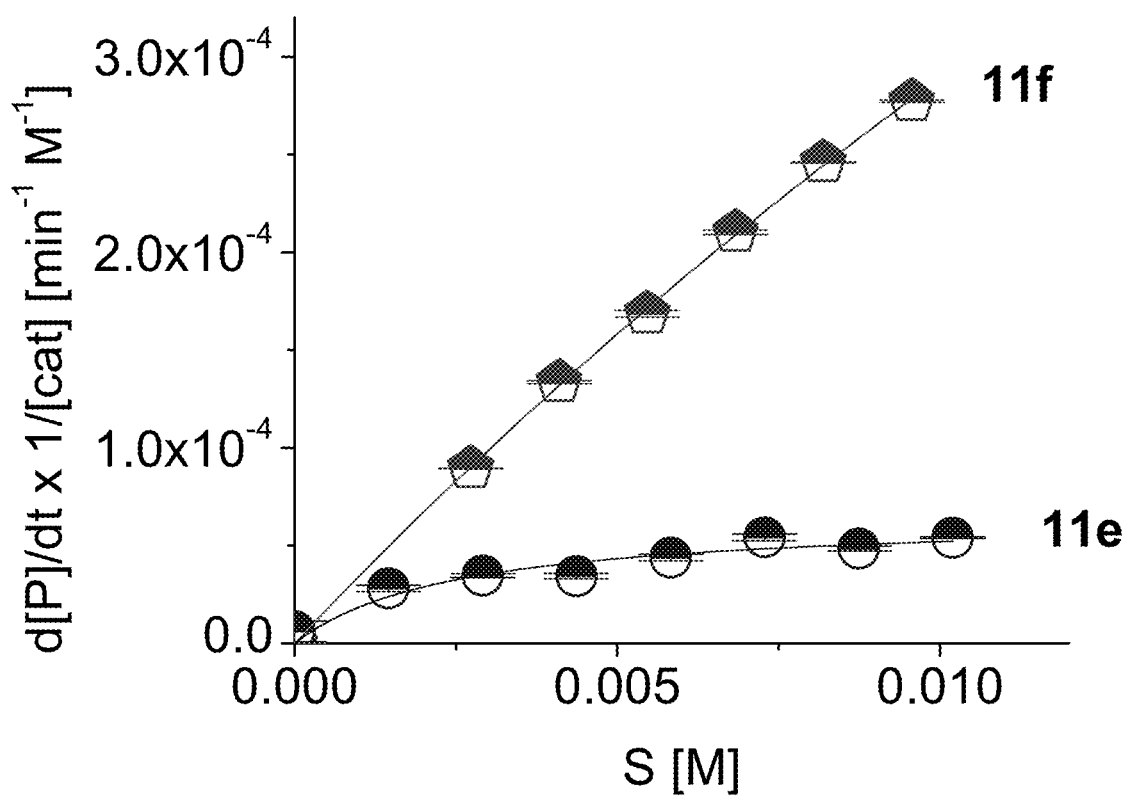
FIG. 4 graphically illustrates product formation during the hydrolysis of 9e and 9f by S-1 in 50 mM HEPES buffer at pH 7.50±0.05 and 30.0±0.1° C.

By contrast, the uncatalyzed reactions of the α- and β-glucosides 9e and 9f are of the same order of magnitude and the chiral complex S-1-catalyzed hydrolyses differ by almost 1.5 orders of magnitude or 28-fold (FIG. 4; Table 2, entries 14 & 17). This observation translates into a 3-fold higher proficiency of chiral complex S-1 to hydrolyze 9e over 9f due to higher substrate affinity of 9f over 9e for chiral complex S-1, and demonstrates the ability of a metal complex to discriminate α- and β-glycosidic bonds notably close to physiological pH. This finding is of particular significance for catalyst development, use of biomass or its transformation into fine chemicals and fuel due to the abundance of α- and β-glucopyranosyl moieties as building blocks in natural products and oligosaccharides including cellulose and starch.

Example 7—Performance of R-1 During Hydrolysis of Glycopyranosides

As elaborated previously, the overall catalyst performance correlates to the intramolecular Cu . . . Cu distance in the metal complex core. As similar rates of the catalyzed substrate hydrolyses are observed for chiral complexes S-1 and R-1 (Table 2), the chirality of the complexes is, however, unlikely to have a profound contribution to the observed discrimination of the epimeric or anomeric model compounds by chiral complex S-1 and is echoed by chiral complex R-1. Instead, the configuration of the hydroxyl groups in the glycon of the substrate presents itself as a rationale for the observed glycoside discrimination. For simplicity, the following discussion on the mechanistic insights is consequently limited to chiral complex S-1.

Example 8—Putative Mechanism of the α-Glycoside Hydrolysis

The high catalytic proficiency of chiral complex S-1 for the hydrolysis of glucopyranosides 9e-f over those of 9a-d indicates again different interactions of the catalyst with the glycon of the substrates. As the epimeric substrates are overall only different in their configuration at C-2 and C-4, respectively, we proposed that the higher acidity of the hydroxyl group at C-2 over that of the hydroxyl group at C-4 and its proximity to the anomeric center promote substrate deprotonation and coordination to the metal complex as pre-requisite for catalytic hydrolysis to occur. The coordination is consequently stronger when a deprotonated cis-diol structure (9a) is participating in metal complex chelation and weaker when a trans-diol structure (9c or 9e) is present accounting for above described observations.

For experimental evidence, the catalytic hydrolysis of substrates 9g and 9h was evaluated. Both substrates are methylated in the glycon at the hydroxyl group at C-2 preventing deprotonation at this position upon interaction with the catalyst, while weaker hydrogen-bonding interactions are still enabled. The hydrolysis of 9g and 9h is unsuccessful with any studied catalyst both at pH 7.5 and in alkaline solution at pH 10.5 indicating that all substrates indeed coordinate to the catalysts over a deprotonated hydroxyl group at C-2. A putative mechanism for the hydrolysis of α-glycoside by chiral complex S-1 at pH 7.5 is deduced from the described experimental observations, and depicted for the hydrolysis of 9a below.

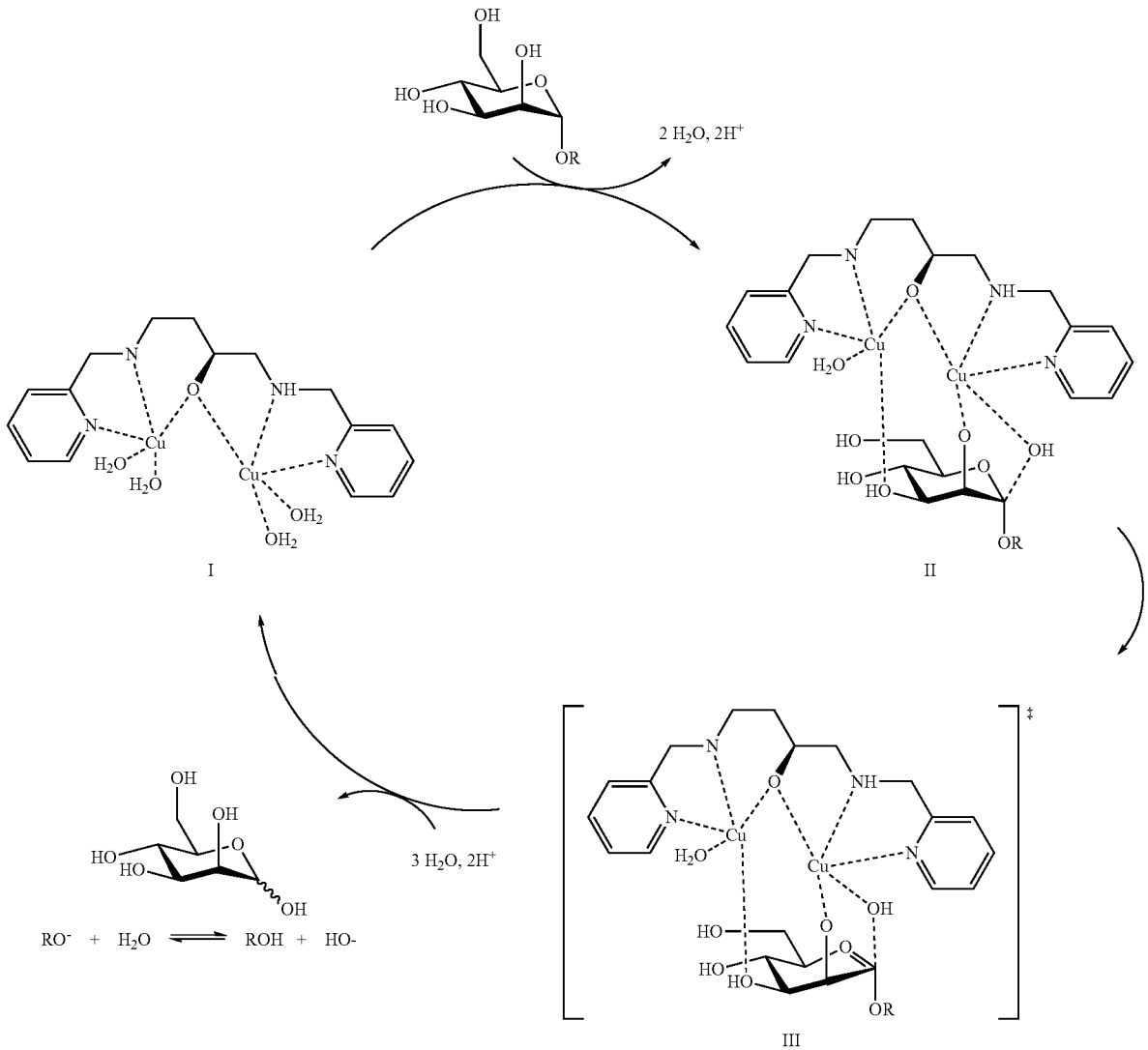

Upon dissolving chiral complexes S-1 and R-1 in solution, a binuclear species I is formed that coordinates the glycoside substrate under release of water and protons resulting in half-acetal formation (Scheme 5, species II). Distortion of the configuration may then yield a structure similar to the transition state proposed for enzymatic glycoside hydrolyses encompassing substrate distortion to a half-chair conformation, $sp^2$-character of the anomeric C-atom, partially positively charged endocyclic 0-atom and lengthening of the glycosidic bond (Scheme 5, species III). Models suggest a twisted boat-like structure for a similar species derived from β-glycosides requiring further computational analyses in future efforts. Hydration of the binuclear copper species and protonation of the sugar by solvent molecules may release the coordinated hydrolysis products to reform species I and close the catalytic cycle.

Example 9—Discrimination of Disaccharides During Catalytic Hydrolysis

Figure 5A:
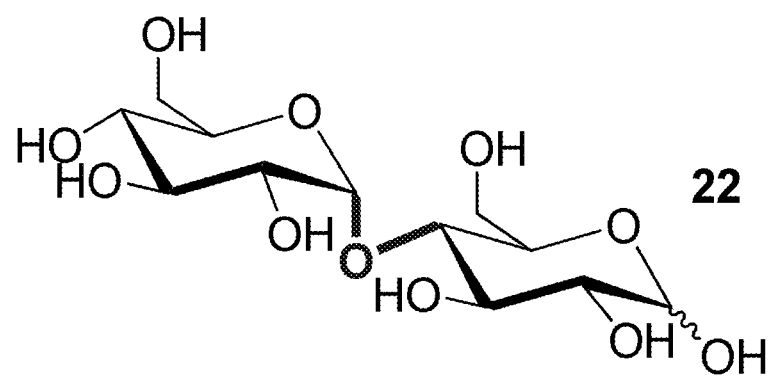
FIG. 5A illustrates various disaccharide structures in accordance with an illustrative embodiment of the invention disclosed herein.
Figure 5A:
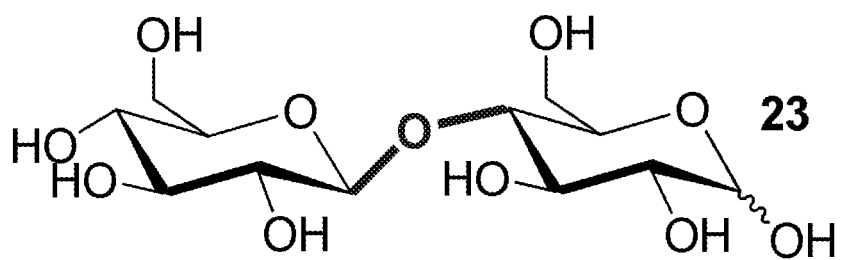
Figure 5A:
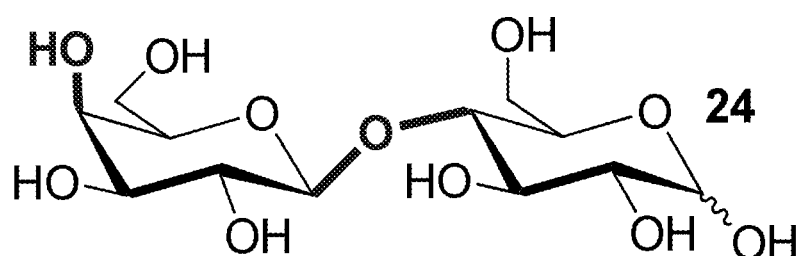
Figure 5B:
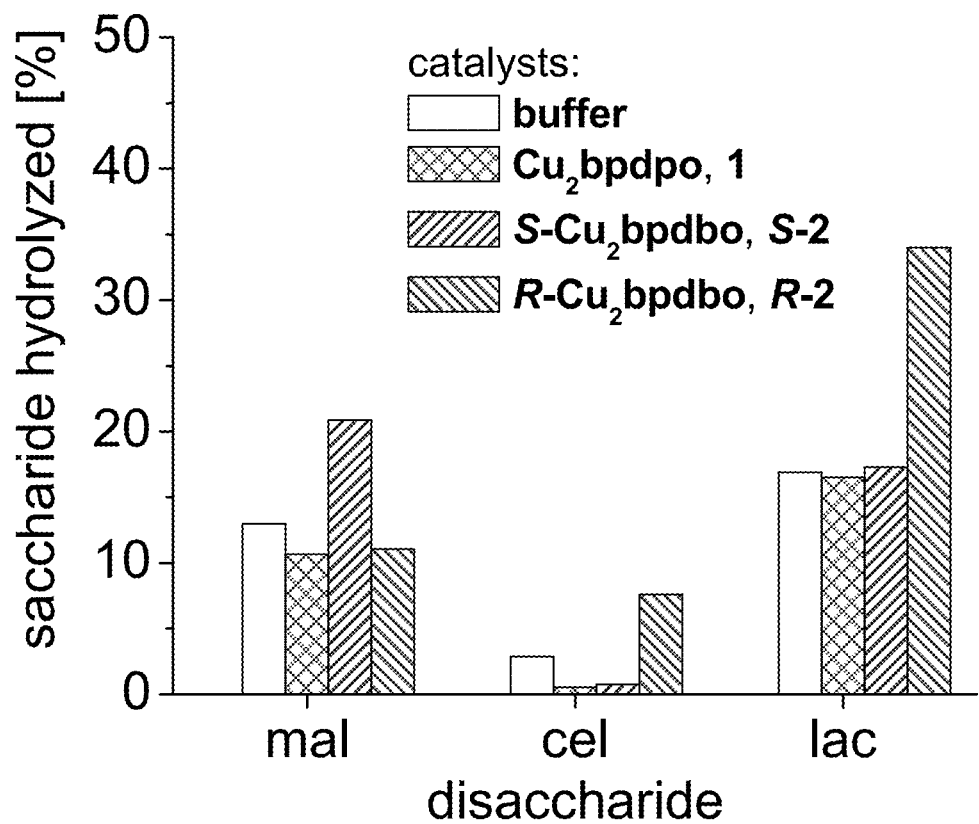
FIG. 5B graphically illustrates catalyzed disaccharide hydrolysis in accordance with an illustrative embodiment of the invention disclosed herein.

In order to apply the catalysts to natural carbohydrates, all complexes were explored in their ability to hydrolyze the disaccharides maltose (9), cellobiose (10), and lactose (11) (FIG. 5a). Disaccharides 9 and 10 differ in the nature of their glycosidic bonds, and 10 and 11 are epimers in their non-reducing sugar moiety. All disaccharides were hydrolyzed at 60° C. at pH 8 over 24 h in presence and absence of 10 mol % of symmetric complex 1, chiral complex S-1, and chiral complex R-1, respectively. The amount of remaining starting material was then quantified by HPLC analysis (FIG. 5b). Evidence for catalyst destruction or sugar oxidation were not apparent under the elaborated conditions. The composition of the complexes is similar to that at pH 7.5 with slightly different amounts of the major catalytically active species.

All experiments were conducted in 100 mM N-[Tris (hydroxymethyl)methyl]-2-aminoethanesul-fonic acid (TES) buffer at pH 8.0 and 60° C. in triplicate, and the obtained data were averaged. The substrate stock solutions were prepared from maltose (9), cellobiose (10) or lactose (11). Typically, 25-30 mg (73-83 mmol) of the disaccharides were dissolved in 1 mL nanopure water yielding 70-83 mM substrate stock solutions. A constant 50 µL aliquot of each stock solution was then used for all experiments. 5 mg of the binuclear metal complexes were dissolved in 10 mL of buffer solution yielding 0.73 mM stock solutions. The catalyst stock solutions were then used in constant 450 µL aliquots for all experiments. The 50 µL aliquot of the substrate stock solutions were diluted with 450 µL nanopure water, buffer or catalyst stock solutions and heated to 60° C. After 24 h, the solutions were cooled in ice, and 100 µL aliquot was taken and 30 mM sodium sulfide solution added. After centrifugation for 5 min at 8.5 g, the supernatant was filtered and subjected to HPLC analysis.

All experiments were conducted on a Shimadzu HPLC with a Rezex-Carbohydrate Na$^+$ (8%) column 300×7.8 mm and 50×7.8 mm guard column (Phenomenex) using nanopure water as eluent isocratic with a flow rate of 0.4 mL/min at 80° C. and ELS detection. The filtered samples were diluted with an equal volume of 50 mM acetic acid buffer at pH 5.0. The resulting solution was subjected to analysis in 25 µL aliquots, and the elution was monitored for 30 min. Disaccharides elute under these conditions between 14-18 min, monosaccharides elute between 20-24 min and the TES buffer elutes at 22.5 min. The area of the peaks in the chromatograms was integrated using the software supplied by Shimadzu. The percentage of hydrolysis for each sugar aliquot was determined by correlation of the area in the respective sample to a reference samples in water.

The data reveal indifference of symmetric complex 1 to hydrolyze the selected disaccharides in any significantly higher amount than buffer solution alone. By contrast, chiral complex S-1 hydrolyzed twice as much of α-glycoside 9 as buffer, symmetric complex 1, or chiral complex R-1. Likewise, chiral complex R-1 hydrolyzed up to 2.5-fold more β-glycosides 10 and 11 than buffer solution or another catalyst. The finding indicates stereoselective discrimination of the glycosidic bonds in disaccharides by the chiral catalysts with a preference of chiral complex S-1 for α-glycosidic bonds and of R-1 for β-glycosidic bonds.

Figure 6:
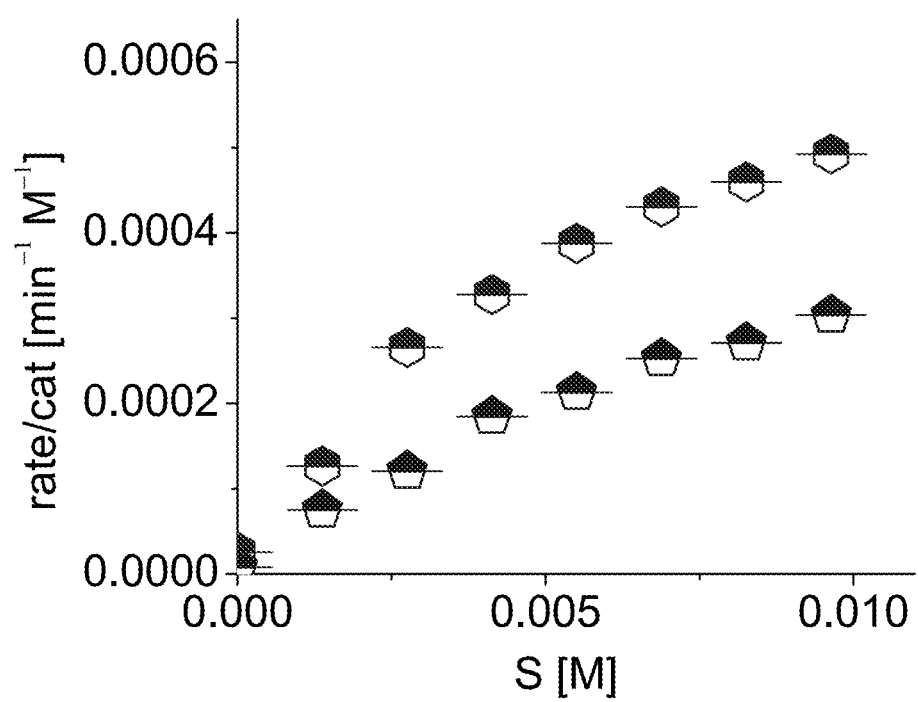
FIG. 6 graphically illustrates catalyzed hydrolysis of 2-chloro-4-nitrophenyl-α-D-mannopyranoside at pH 7.5 in 50 mM HEPES buffer; $Cu_2$bpdpo (red) ($k_{cat}$=8.1±0.9 $10^{-4}$ $min^{-1}$; $K_M$=12.0±2.3 mM); $Zn_2$tpdpo (blue) ($k_{cat}$=6.4±0.6× $10^{-4}$ $min^{-1}$; $K_M$=11.0±1.6 mM; $k_{non}$=4.4×$10^{-7}$ $min^{-1}$ $M^{-1}$).

Example 10—Performance of Binuclear Zn (II) Complexes During Hydrolysis of Glycopyranosides FIG. 6 illustrates catalyzed hydrolysis of 2-chloro-4-nitrophenyl-α-D-mannopyranoside at pH 7.5 in 50 mM HEPES buffer, with Cu$_2$bpdpo (red) ($k_{cat}$=8.1±0.9 10$^{-4}$ min$^{-1}$; $K_M$=12.0±2.3 mM) and Zn$_2$tpdpo (blue) ($k_{cat}$=6.4±0.6×10$^{-4}$ min$^{-1}$; $K_M$=11.0±1.6 mM; $k_{non}$=4.4×10$^{-7}$ min$^{-1}$ M$^{-1}$).

Whereas, the compounds and methods have been described in relation to the drawings and claims, it should be understood that other and further modifications and formulations, apart from those shown or suggested herein, may be made within the scope of this invention.

What is claimed is:

1. A method of hydrolysis of saccharides and glycosides, said method comprising the steps of:
    discriminating α glycosidic bonds of saccharides in aqueous solutions using an enantiopure asymmetric chiral binuclear transition metal (II) complex wherein the formula of said enantiopure asymmetric chiral binuclear transition metal (II) complex is:

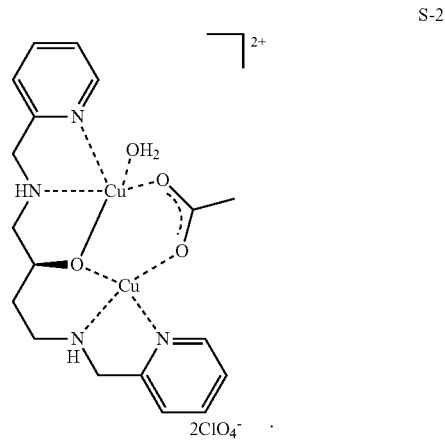

2. The method of claim 1 further comprises the step of discriminating said α-glycosidic bonds of saccharides in aqueous solutions at a pH range from 7.45 to 7.55 using said chiral binuclear transition metal (II) complex.

* * * * *